US009615623B2

(12) United States Patent
Hurd et al.

(10) Patent No.: US 9,615,623 B2
(45) Date of Patent: Apr. 11, 2017

(54) ANKLE AND FOOT SUPPORT SYSTEM

(71) Applicant: NIKE, Inc., Beaverton, OR (US)

(72) Inventors: John Hurd, Lake Oswego, OR (US); Clifford B. Gerber, West Linn, OR (US)

(73) Assignee: NIKE, Inc., Beaverton, OR (US)

( * ) Notice: Subject to any disclaimer, the term of this patent is extended or adjusted under 35 U.S.C. 154(b) by 416 days.

(21) Appl. No.: 14/299,557

(22) Filed: Jun. 9, 2014

(65) Prior Publication Data

US 2014/0338227 A1 Nov. 20, 2014

Related U.S. Application Data

(62) Division of application No. 13/305,960, filed on Nov. 29, 2011, now Pat. No. 8,747,340.

(51) Int. Cl.
| | | |
|---|---|---|
| *A43C 11/16* | (2006.01) | |
| *A43B 7/20* | (2006.01) | |
| *A61F 5/01* | (2006.01) | |
| *A43B 3/24* | (2006.01) | |
| *A43B 5/18* | (2006.01) | |

(52) U.S. Cl.
CPC ............... *A43B 7/20* (2013.01); *A43B 3/242* (2013.01); *A43B 5/18* (2013.01); *A43C 11/165* (2013.01); *A61F 5/0111* (2013.01)

(58) Field of Classification Search
CPC ...................................................... A43B 7/20
USPC . 602/65, 62, 61, 60, 41, 27, 23, 5, 1; 36/45, 36/50.1, 50.5, 56
See application file for complete search history.

(56) References Cited

U.S. PATENT DOCUMENTS

| | | | |
|---|---|---|---|
| 1,183,001 A | 5/1916 | Gleason | |
| 1,265,280 A | 5/1918 | Tweedie | |
| 1,483,782 A | 2/1924 | Cole | |
| 1,634,576 A | 7/1927 | Hogan | |
| 4,142,307 A * | 3/1979 | Martin | A43B 5/0447 24/68 SK |
| 4,503,566 A | 3/1985 | Wheeler | |
| 4,711,042 A | 12/1987 | Morell et al. | |
| 4,748,726 A * | 6/1988 | Schoch | A43C 11/16 24/68 B |
| 5,640,787 A * | 6/1997 | Spademan | A43B 5/0441 36/117.3 |
| 5,791,021 A * | 8/1998 | James | A43C 1/003 24/68 SK |
| 5,819,439 A | 10/1998 | Sanchez | |
| 5,822,887 A | 10/1998 | Turner | |

(Continued)

OTHER PUBLICATIONS

Non-Final Office Action mailed Jun. 13, 2016 for U.S. Appl. No. 14/297,983, 26 pages.

(Continued)

*Primary Examiner* — Tarla Patel
(74) *Attorney, Agent, or Firm* — Plumsea Law Group, LLC

(57) ABSTRACT

Methods and systems relating to an ankle and foot support system are disclosed. In some embodiments, a covering having a cable tightening mechanism may be associated with a cable that is slidably engaged with the cover. In some embodiments, the cable may be slidably engaged with a tube guide that is attached to the cover. In some embodiments, the cable may form an exposed loop that associates with a loop receiving member. In some embodiments, the loop receiving member may be attached to the cover.

20 Claims, 21 Drawing Sheets

(56) References Cited

U.S. PATENT DOCUMENTS

| | | | |
|---|---|---|---|
| 6,267,390 B1* | 7/2001 | Maravetz | A43B 5/0401 |
| | | | 280/14.21 |
| 6,289,558 B1 | 9/2001 | Hammerslag | |
| 6,347,436 B1* | 2/2002 | Barber | A43C 1/00 |
| | | | 24/68 SK |
| 6,416,074 B1 | 7/2002 | Maravetz et al. | |
| 6,467,195 B2 | 10/2002 | Pierre et al. | |
| 6,922,917 B2* | 8/2005 | Kerns | A43B 5/14 |
| | | | 36/50.1 |
| 7,328,527 B2 | 2/2008 | Goldman | |
| 7,428,787 B2 | 9/2008 | Crowley, II et al. | |
| 7,591,050 B2 | 9/2009 | Hammerslag | |
| 7,806,842 B2 | 10/2010 | Stevenson et al. | |
| 8,381,362 B2 | 2/2013 | Hammerslag et al. | |
| 8,747,340 B2 | 6/2014 | Gerber et al. | |
| 2005/0160627 A1* | 7/2005 | Dalgaard | A43B 5/0401 |
| | | | 36/50.5 |
| 2005/0284003 A1* | 12/2005 | Dalgaard | A43B 5/0401 |
| | | | 36/50.5 |
| 2006/0156517 A1 | 7/2006 | Hammerslag et al. | |
| 2008/0066272 A1 | 3/2008 | Hammerslag et al. | |
| 2009/0071037 A1 | 3/2009 | Foxen et al. | |
| 2011/0197362 A1* | 8/2011 | Chella | A61F 5/0111 |
| | | | 5/650 |
| 2013/0138028 A1 | 5/2013 | Gerber et al. | |
| 2013/0138029 A1 | 5/2013 | Gerber et al. | |
| 2015/0374526 A1 | 12/2015 | Hurd et al. | |

OTHER PUBLICATIONS

Notice of Allowance mailed Mar. 12, 2015 in U.S. Appl. No. 13/305,973.
Restriction Requirement mailed Jun. 25, 2013 in U.S. Appl. No. 13/305,960.
Response to Restriction Requirement filed Jul. 24, 2013 in U.S. Appl. No. 13/305,960.
Office Action mailed Sep. 10, 2013 in U.S. Appl. No. 13/305,960.
Amendment filed Dec. 11, 2013 in U.S. Appl. No. 13/305,960.
Supplemental Amendment filed Jan. 14, 2014 in U.S. Appl. No. 13/305,960.
Notice of Allowance mailed Jan. 29, 2014 in U.S. Appl. No. 13/305,960.
Non-Final Office Action mailed Jul. 11, 2016 for U.S. Appl. No. 14/299,302, filed Jun. 9, 2014.

* cited by examiner

ANKLE AND FOOT SUPPORT SYSTEM

CROSS-REFERENCE TO RELATED APPLICATIONS

This application is a divisional of Gerber et al., U.S. Patent Application Publication No. 2013/0138028, published on May 30, 2013 and entitled "Ankle and Foot Support System," the entire disclosure of which is incorporated herein by reference.

BACKGROUND

The current embodiments relate generally to athletic support equipment. More specifically, the current embodiments relate to systems and methods for supporting an ankle and foot.

Various types of athletic sports equipment have been previously proposed for use in a variety of applications. Sports participants, football players for example, may desire additional support to the ankle and foot region in order to help prevent injuries to the ankle and/or foot. Conventional methods for providing foot and ankle support include athletic tape wrapped around the ankle region as well as the foot. However, there are several disadvantages to conventional taping methods. For example, taping ankles often requires the skills of an athletic trainer in order to be properly applied, which can be expensive. In addition, conventional taping methods are time consuming and are not adjustable once they have been applied. The amount of ankle support provided by conventional taping methods are not consistent and may vary with each application since a new tape wrap must be applied before each athletic event. Even after conventional taping methods have been applied, the taping may still lack the desired stiffness and support to the ankle and/or foot region.

SUMMARY

Methods and systems relating to an ankle and foot support system are disclosed. In some embodiments, a covering having a cable tightening mechanism may be associated with a cable that is slidably engaged with the cover. In some embodiments, the cable may be slidably engaged with a tube guide that is attached to the cover. In some embodiments, the cable may form an exposed loop that associates with a loop receiving member. In some embodiments, the loop receiving member may be attached to the cover.

In one aspect, an ankle and foot support system is disclosed. In one embodiment, the ankle and foot support system may include a covering having an outer surface. In some embodiments, the ankle and foot support system may also include a tube guide attached to the outer surface of the covering. In some embodiments, the ankle and foot support system may also include a cable tightening mechanism attached to the outer surface of the covering. In some embodiments, the ankle and foot support system may also include a cable wherein a first portion of the cable is slidably engaged with the tube guide. In some embodiments, a second portion of the cable may be associated with the cable tightening mechanism.

In another aspect, an ankle and foot support system is disclosed. In one embodiment, the ankle and foot support system may include a covering having an outer surface. In some embodiments, the ankle and foot support system may also include a cable tightening mechanism rotatably attached to the outer surface of the covering. In some embodiments, the ankle and foot support system may also include a cable, wherein a first portion of the cable is slidably engaged with the covering, wherein a second portion of the cable is associated with the cable tightening mechanism. In some embodiments, the ankle and foot support system may also include a loop receiving member attached to the outer surface of the covering, wherein a third portion of the cable forms an exposed loop, wherein the loop receiving member is adapted to receive the exposed loop.

In another aspect, an ankle and foot support system is disclosed. In one embodiment, the ankle and foot support system may include a covering having an outer surface. In some embodiments, the ankle and foot support system may also include a bottom strap having an outer surface extending from the covering, the bottom strap forming an opening adapted to receive a portion of an article of footwear. In some embodiments, the ankle and foot support system may also include a cable tightening mechanism attached to the outer surface of the covering. In some embodiments, the ankle and foot support system may also include a tube guide attached to the outer surface of the bottom strap. In some embodiments, the ankle and foot support system may also include a cable, wherein a first portion of the cable is slidably engaged within the tube guide. In some embodiments, a second portion of the cable may be associated with the cable tightening mechanism.

In another aspect, a method of providing support to an ankle and foot is disclosed. In one embodiment, the method of providing support to an ankle and foot may include positioning a portion of a covering over a portion of an article of footwear. In some embodiments, the method of providing support to an ankle and foot may also include positioning an exposed loop that is slidably engaged with the covering onto a loop receiving member located on an outer surface of the covering. In some embodiments, the method of providing support to an ankle and foot may also include adjusting a cable tightening mechanism attached to the outer surface of the covering, the cable tightening mechanism associated with the exposed loop.

Other systems, methods, features and advantages of the current embodiments will be, or will become, apparent to one of ordinary skill in the art upon examination of the following figures and detailed description. It is intended that all such additional systems, methods, features and advantages be included within this description and this summary, be within the scope of the current embodiments, and be protected by the following claims.

BRIEF DESCRIPTION OF THE DRAWINGS

The current embodiments can be better understood with reference to the following drawings and description. The components in the figures are not necessarily to scale, emphasis instead being placed upon illustrating the principles of the current embodiments. Moreover, in the figures, like reference numerals designate corresponding parts throughout the different views.

DETAILED DESCRIPTION

Figure 1:
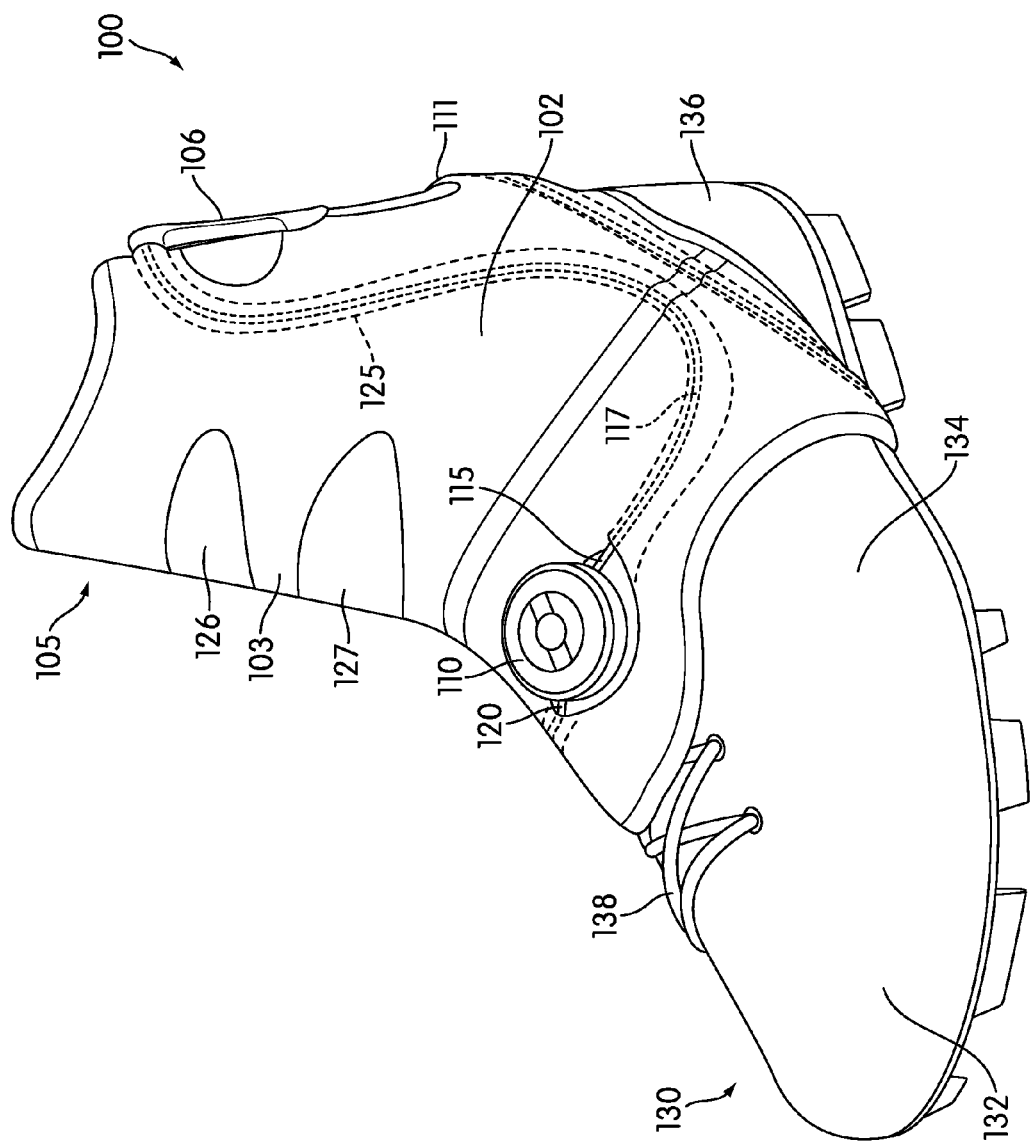
FIG. 1 is a perspective view of an embodiment of an ankle support system in the closed position.

Various embodiments of ankle support systems and methods are disclosed. In some embodiments, as seen in FIG. 1, an ankle support system 100 may include provisions for a protective covering 105 placed over a portion of the wearer's foot, ankle and/or leg. In some embodiments, the covering 105 may also be placed over a portion of an article of footwear 130.

Conventional articles of footwear include two primary elements, an upper and a sole structure. The upper may form a layer over the foot that comfortably receives and securely positions the foot with respect to the sole structure. The sole structure may be secured to a lower portion of the upper and may be generally positioned between the foot and the ground. In addition to attenuating ground reaction forces (i.e., providing cushioning) during walking, running, and other ambulatory activities, the sole structure may influence foot motions (e.g., by resisting pronation), impart stability, allow for twisting and bending, and provide traction, for example. Accordingly, the upper and the sole structure may operate cooperatively to provide a comfortable structure that is suited for a wide variety of athletic activities.

The upper may be formed from a plurality of material elements (e.g., textiles, polymer sheets, foam layers, leather, synthetic leather) that may be stitched or adhesively bonded together to form a void on the interior of the footwear for comfortably and securely receiving a foot. More particularly, the upper may form a structure that extends over instep and toe areas of the foot, along medial and lateral sides of the foot, and around a heel area of the foot. The upper may also incorporate a lacing system to adjust the fit of the footwear, as well as permitting entry and removal of the foot from the void within the upper. In addition, the upper may include a tongue that extends under the lacing system to enhance adjustability and comfort of the footwear, and the upper may incorporate a heel counter.

An upper may be depicted as having a substantially conventional configuration incorporating a plurality of material elements (e.g., textiles, foam, leather, and synthetic leather) that are stitched or adhesively bonded together to form an interior void for securely and comfortably receiving a foot. The material elements may be selected and located with respect to the upper in order to selectively impart properties of durability, air-permeability, wear-resistance, flexibility, and comfort, for example. In some embodiments, an ankle opening in the heel region provides access to the interior void. In some embodiments, the upper may include a lace that is utilized in a conventional manner to modify the dimensions of the interior void, thereby securing the foot within the interior void and facilitating entry and removal of the foot from the interior void. The lace may extend through apertures in the upper, and a tongue portion of the upper may extend between the interior void and the lace. Given that various aspects of the present discussion primarily relate to the sole structure, the upper may exhibit the general configuration discussed above or the general configuration of practically any other conventional or non-conventional upper. Accordingly, the overall structure of the upper may vary significantly.

In some embodiments, the covering 105 may be disposed around the sole structure, in addition to the upper. In some embodiments, sole structure may be secured to the upper and has a configuration that extends between the upper and the ground. In addition to attenuating ground reaction forces (i.e., cushioning the foot), the sole structure may provide traction, impart stability, and limit various foot motions, such as pronation.

The term "covering" as used throughout this specification and claims refers to any structure that wraps or encloses a portion of a foot, leg, ankle, and/or article of footwear. In some embodiments, covering may refer to a spat that is adapted to be positioned over an article of footwear once the wearer's foot has been positioned inside the article of footwear. A covering may be made of any material or substance that allows the covering to be positioned over the wearer's foot, leg, ankle, and/or article of footwear.

The covering 105 may be manufactured using one or more of a variety of different suitable materials known in the art. In some embodiments, the covering 105 may be manufactured from an elastic neoprene material. An elastic neoprene material may provide suitable elasticity and strength, and may be wrapped easily to provide the controllable tension to the foot, leg, and ankle of the user. In some embodiments, the covering 105 may be made from a lycra material. In some embodiments, the covering 105 may include waterproof material, such as a waterproof layer, coating, or film. In some embodiments, the covering 105 may include a breathable material, which may contain perforations or other such structures enhancing breathability. In some embodiments, the covering 105 may include an abrasion resistant material, such as an abrasion resistant layer, coating, or film.

In some embodiments, indicia may be located on a visible surface of the covering 105. For example, a player's name, number, team graphics, colors or other type of indicia may be visible when the covering 105 is placed over an article of footwear 130. In some embodiments, the covering 105 may be a single connected piece made from several separate pieces of material sewn together. For example, some embodiments may include one or more layers, with each layer manufactured from a material having different properties. However, in other embodiments, the covering 105 may be made of multiple pieces, or may be a single, integral piece. In some embodiments, a surface of the covering 105 may include a surface pattern containing geometric shapes raised from the surface of the covering 105. In other embodiments, the surface pattern may be flush with surface of the covering 105.

The ankle support system 100 disclosed has a general configuration suitable for soccer or football. Concepts associated with the ankle support system 100 may also be applied to a variety of other athletic footwear types, including running shoes, baseball shoes, basketball shoes, cross-training shoes, cycling shoes, football shoes, golf shoes, tennis shoes, walking shoes, and hiking shoes and boots, for example. The concepts may also be applied to footwear types that are generally considered to be non-athletic, including dress shoes, loafers, sandals, and boots. Accordingly, the concepts disclosed herein apply to a wide variety of footwear types.

For consistency and convenience, directional adjectives are employed throughout this detailed description corresponding to the illustrated embodiments. The term "longitudinal" as used throughout this detailed description and in the claims refers to a direction extending a length of a component, such as a sole structure. In some cases, the longitudinal direction may extend from a forefoot portion to a heel portion of the component. Also, the term "lateral" as used throughout this detailed description and in the claims refers to a direction extending a width of a component. In other words, the lateral direction may extend between a medial side and a lateral side of the component, or along the width of the component. The terms longitudinal and lateral can be used with any component of an article of footwear, including a sole structure as well as individual components of the sole structure.

In some embodiments of an ankle support system 100, provisions may be provided for a covering 105 having different regions or zones of flexibility and/or rigidity. In some embodiments, the covering 105 may include one or more layers of material having different properties relating to rigidity and/or flexibility. In some embodiments, rigid material may be included in regions where additional support is desired. For example, some embodiments may include material made from carbon fibers and/or glass fibers in areas where more rigidity is desired. In other embodiments, rigid material may be excluded or minimized in areas or zones where more flexibility is desired. For example, some embodiments may include layers where rigid material has been cut out or removed from the regions or zones where a higher degree of flexibility is desired. In other embodiments, the thickness of the rigid material may be reduced in areas where more flexibility is desired.

In some embodiments of an ankle support system 100, ventilation may be provided throughout different areas, or zones, of the covering 105, in order to remove humidity trapped near the foot. In some embodiments, ventilation may be provided by holes, channels and/or cut out portions in one or more layers of the covering 105. In some embodiments, the holes, channels, or cut out portions that provide ventilation may also provide regions or zones of flexibility. However, in other embodiments, the regions providing ventilation may be separate from the regions that provide increased flexibility.

In some embodiments, as shown in FIG. 1, the covering 105 may include a first cut out region 126 and a second cut out region 127. In some embodiments, the first cut out region 126 and/or second cut out region 127 may provide for ventilation for humidity trapped near the foot. In some embodiments, the first cut out region 126 and/or second cut out region 127 may provide for a zone or region of increased flexibility. In some embodiments, the first cut out region 126 and/or second cut out region 127 may provide for ventilation in addition to a region of increased flexibility. Although the first cut out region 126 and second cut out region 127 are generally elongated in shape, the first cut out region 126 and second cut out region 127 may be any shape. For example, the first cut out region 126 and second cut out region 127 may generally be, but not limited to, circular, square, rectangular, or any other geometric shape. Although FIG. 1 shows a first cut out region 126 and second cut out region 127, other embodiments may include more or less cut out regions.

FIG. 1 shows a covering 105 surrounding a portion of an article of footwear 130. In some embodiments, the covering 105 may be in contact with at least a portion of the forefoot region 132, the midfoot region 134 and/or the heel region 136 of the article of footwear 130. In some embodiments, a portion of the covering 105 may contact a portion of the laces region 138 of the article of footwear 130. In other embodiments, a portion of the covering 105 may contact the entire laces region 138 of the article of footwear 130.

In some embodiments of an ankle support system 100, provisions may be included for securing the covering 105 around a portion of an article of footwear 130. For example, some embodiments may include provisions for preventing the covering 105 from shifting or moving during athletic activity. In some embodiments, the covering 105 may include one or more components that hold the covering 105 securely in place in a variety of different manners. In some embodiments, fasteners or straps may be used to securely position the covering 105. In some embodiments, clasps, buttons, snaps, buckles, hooks, adhesives, or other structure known in the art may be used to securely the position the covering 105 in place. In some embodiments, fastener portions may be held in place by hook and loop fasteners (such as Velcro) located on a surface of the fastener portion, as well as surfaces that receive the fastener portions.

Figure 3:
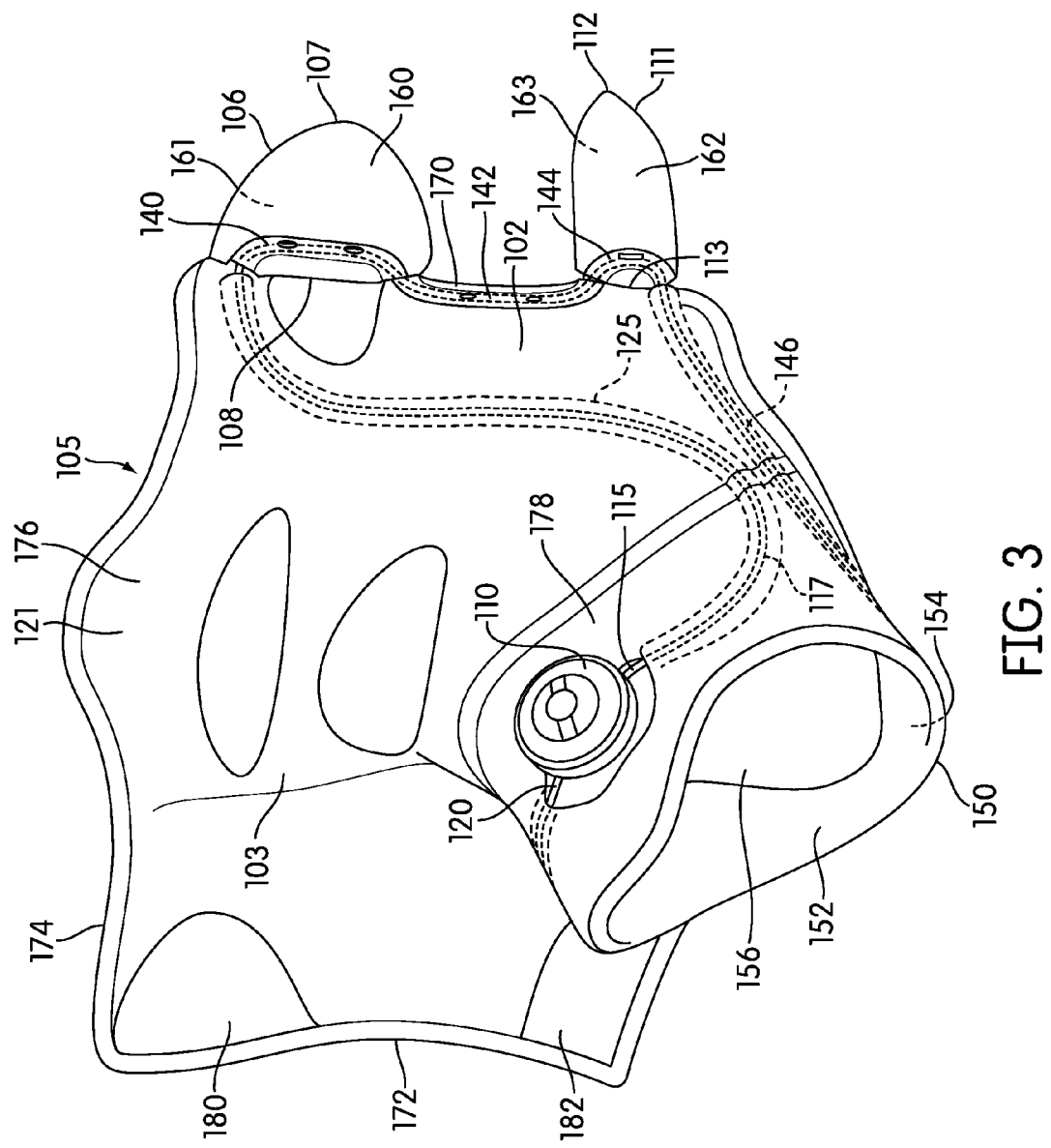
FIG. 3 is a perspective view of an embodiment of a covering in the open position.

FIGS. 1 and 3 show a first fastener 106 for securing the covering 105 in place. FIG. 3 shows the covering 105 in an open position, where the covering 105 is positioned to receive at least a portion of the article of footwear 130. Referring to FIG. 3, the first fastener 106 may be located on the lateral side 102 of the covering 105, and may be adjacent to the lateral side edge 170 of the covering 105. The first fastener 106 may include a first end 107 that is distal to the lateral side edge 170 and a second end 108 that is proximate to the lateral side edge 170. In some embodiments, the second end 108 is hingedly attached to the lateral side edge 170 by any manner known in the art. For example, the second end 108 may be sewn, affixed, adhered, snapped, buckled and/or fastened to a location proximate to lateral side edge 170. The first fastener 106 may also include a first surface 160 and a second surface 161. In some embodiments, the second surface 161 may include hook and loop fasteners (such as Velcro). In other embodiments, the second surface may include any other fasteners known in the art.

In some embodiments, a first fastener receiving portion 180 may be adapted to receive the second surface 161 of the first fastener 106. Referring to FIG. 3, a first fastener receiving portion 180 may be located on the medial side 103 of the covering 105, and may be adjacent to the medial side edge 172 of the covering 105. In some embodiments, the second surface 161 of the first fastener 106 and the first fastener receiving portion 180 may include hook and loop fasteners (such as Velcro). However, first fastener receiving portion 180 may be adapted to receive the second surface 161 of the first fasteners 106 in any manner known in the art.

In addition to the first fastener 106, the covering may also include a second fastener 111. In some embodiments, the second fastener 111 may be located on the lateral side 102 of the covering 105, and may be adjacent to the lateral side edge 170 of the covering 105. The second fastener 111 may include a first end 112 that is distal to the lateral side edge 170 and a second end 113 that is proximate to the lateral side edge 170. In some embodiments, the second end 113 is hingedly attached to the lateral side edge 170 by any manner known in the art. For example, the second end 113 may be sewn, affixed, adhered, snapped, buckled and/or fastened to the lateral side edge 170. The second fastener 111 may include a first surface 162 and a second surface 163. In some embodiments, the second surface 163 may include hook and loop fasteners (such as Velcro). In other embodiments, the second surface may include any other fasteners known in the art.

In some embodiments, a second fastener receiving portion 182 may be adapted to receive the second surface 163 of the second fastener 111. Referring to FIG. 3, a second fastener receiving portion 182 may be located on the medial side 103 of the covering 105, and may be adjacent to the medial side edge 172 of the covering 105. In some embodiments, the second fastener receiving portion 182 may include hook and loop fasteners (such as Velcro). However, second fastener receiving portion 182 may be adapted to receive the second surface 163 of the second fastener 111 in any manner known in the art. Although FIGS. 1-6 describe a covering 105 having two fasteners and two fastener receiving portions, other embodiments may include more or less fasteners and/or fastener receiving portions.

Once the covering 105 has been positioned around the ankle, leg, and/or article of footwear 130, the covering 105 may then be arranged into a closed condition to securely fasten the covering 105 in place. FIG. 1 shows the covering 105 in a closed condition, where the covering 105 has been positioned over a portion of the article of footwear 130. The first fastener 106 and second fastener 111 on the lateral side 102 of the covering 105 are attached to the first fastener receiving portion 180 and second fastener receiving portion 182, respectively, on the medial side 103 of the covering 105.

Some embodiments of an ankle support system 100 may include provisions for adjusting the tightness of the covering 105 once the covering 105 has been arranged into a closed condition around the article of footwear 130. In some embodiments, cables may be slidably engaged with the covering 105 and may be tightened using a tightening mechanism in order to adjust the desired tension. The cable may be made of any material known in the art, such as metals, textiles, fiber components, or the like. The cable may have any size or shape known in the art, for example, a single filament, separate filaments bound or braided together, or may include a flat ribbon of material. When a single portion of material is used for cable, the ends of the cable may be attached to each other to form a closed loop. In some embodiments, the ends of the cable may be attached to each other using any method known in the art, such as using a mechanical connector, an adhesive, or by welding or the like.

In some embodiments, the configuration of the cable throughout the covering 105 may vary. In some embodiments, cables or strings may be located between one or more layers of the covering 105. In some embodiments, the cables or strings are allowed to move freely between the layers of the covering 105. In other embodiments, the cables or strings may be attached to at least one surface of one or more layers of the covering 105. In other embodiments, the cables or strings may be located within tube guides.

The term "tube guides," as used throughout this specification and claims, refers to any structure or channel that slidably receives a cable. In some embodiments, a tube guide may be a tube that has been attached to a surface. The tube may be formed from plastic, neoprene, or any other material known in the art. In other embodiments, a tube guide may be formed by attaching a strip of material onto a surface forming a channel so that a cable is slidably received within the channel. In some embodiments, a tube guide may include both a strip of material and a tube, wherein the strip of material surrounds the tube and the strip of material and/or tube is attached to a surface.

In some embodiments, the cable may be associated with a cable tightening mechanism 110. In some embodiments, the cable tightening mechanism 110 may be associated with a portion of a cable 117 having a first end and second end that are connected, forming a continuous loop that may be slidably engaged with the covering 105. In other embodiments, the cable tightening mechanism 110 may be associated with a portion of a cable 117 having a first and second end that are fixedly attached to the covering 105, while the remaining portions of the cable 117 may be slidably engaged with the covering 105. In still further embodiments, the cable tightening mechanism 110 may be associated with a portion of a cable 117 having a first and second end that are connected to one another, wherein some portions of the cable 117 may be fixedly attached to the covering 105 and other portions may be slidably engaged with the covering 105.

In some embodiments, the cable tightening mechanism 110 may vary. For example, in some embodiments, the cable tightening mechanism 110 may be a knot that secures one cable portion to another cable portion in order to shorten the effective length of the loop. In other embodiments, as will be discussed in more detail in FIGS. 21-23, the cable tightening mechanism 110 may include a cam lever system. In other embodiments, a cable tightening mechanism 110 may be any mechanical device that shortens the effective length of the cable 117. In some embodiments, a cable tightening mechanism 110 may be a reel that may be rotated in order to wrap the cable 117 around the reel to shorten the effective length of the cable.

FIG. 1 shows one embodiment for adjusting the tightness of covering 105 once the covering 105 has been arranged into a closed condition around the article of footwear 130. Referring to FIG. 1, the tightness of the covering 105 may generally be tightened using a cable 117 and a cable tightening mechanism 110. The cable 117 may form one continuous loop that may be slidably engaged with the covering 105.

The cable tightening mechanism 110 may be disposed anywhere on the outer surface 121 of the covering 105. In some embodiments, the cable tightening mechanism 110 may be positioned in the center of the back of the covering 105. This position may prevent or inhibit accidentally activating the cable tightening mechanism 110 while wearing the covering 105. In other embodiments, the cable tightening mechanism 110 may be disposed on a lateral side 102 of the covering 105. Disposing the cable tightening mechanism 110 on the lateral side 102 of the covering 105 may minimize the contact between the cable tightening mechanism 110 and other obstacles, such as players or the ball. In some embodiments, the cable tightening mechanism 110 may be located on the front of the covering 105. In other embodiments, the cable tightening mechanism 110 may be disposed on the front of the covering 105, to allow the wearer to easily adjust the tension when using the cable tightening mechanism 110.

In some embodiments, as seen in FIGS. 1 and 3, a cable 117 may be associated with the cable tightening mechanism 110. In some embodiments, the cable 117 may include a first segment 115, generally located on the lateral side 102 of the covering 105, and a second segment 120, generally located on the medial side 103 of the covering 105.

Any suitable cable tightening mechanism 110 may be used, and the cable tightening mechanism 110 may be any type of mechanism known in the art. Some embodiments may use one or more aspects of the cable tightening systems disclosed in Hammerslag, U.S. Pat. No. 7,591,050, which is hereby incorporated by reference in its entirety. In addition, or in the alternative, some embodiments may also use one or more aspects of the cable tightening systems disclosed in Hammerslag, U.S. Pat. No. 6,289,558, which is hereby incorporated by reference in its entirety.

Figure 2:
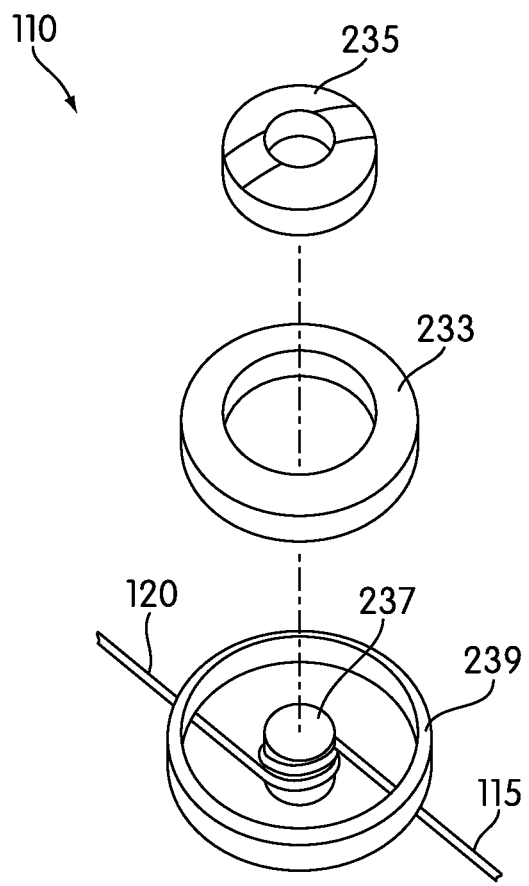
FIG. 2 is an exploded view of an embodiment of a cable tightening mechanism.

FIG. 2 shows an exploded view of one embodiment of the cable tightening mechanism 110. As shown in FIG. 2, the cable tightening mechanism 110 may include a handle 233 generally positioned around an exterior of the cable tightening mechanism 110, a top 235 generally positioned in the center of the handle 233, a spindle 237 generally positioned underneath the top 235, and a track 239 generally positioned within handle 233. Referring to FIG. 2, a first segment 115 and second segment 120 of cable 117 may be fed into the cable tightening mechanism 110 and wound around the spindle 237. Spindle 237 may be rotatably mounted to a surface of the covering 105 so that turning the spindle 237 in a first direction may wind more of the first segment 115 and second segment 120 of the cable around the spindle 237, thereby decreasing the effective length of the cable 117. In some embodiments, turning the spindle 237 in a second direction may unwind the first segment 115 and second segment 120, thereby increasing the effective length of the cable 117. In some embodiments, the first direction will be clockwise, and the second direction will be counter-clockwise. In other embodiments, the first direction will be counter-clockwise, and the second direction will be clockwise. Top 235 may be used to prevent damage to spindle 237 and to retain spindle 237 and cable 117 in position.

In some embodiments, spindle 237 may be attached to handle 233. Handle 233 may be used to turn spindle 237 in the first direction, the direction that will wind cable 117. Handle 233 may ride on track 239 to maintain smooth movement of handle 233. When handle 233 is turned, spindle 237 may also be turned in the same direction to wind cable 117. Spindle 237 may be ratcheted so that handle 233 may only turn spindle 237 in one direction. Further, the ratcheting of spindle 237 may lock spindle 237 in position so that the desired length of cable 117 may be maintained. As will be discussed in further detail in FIG. 7, pulling out cable tightening mechanism 110 may release the locking of spindle 237. In some embodiments, spindle 237 may be spring-loaded so that when the cable tightening mechanism 110 is pulled away from covering 105 to release the locking of spindle 237, spindle 237 will turn in the second direction, or the direction that unwinds cable 117.

FIG. 3 illustrates one embodiment of a covering 105 having a cable 117 that is slidably engaged within tube guides located on a surface of the covering 105. As discussed in FIGS. 1 and 2, a continuous loop of cable 117 may be wrapped around the cable tightening mechanism 110. In some embodiments, the cable 117 may include a first segment 115, generally located on the lateral side 102 of the covering 105, and a second segment 120, generally located on the medial side 103 of the covering 105.

Referring to FIG. 3, the first segment 115 of the cable 117 may be slidably engaged with a first tube guide 125 attached to the outer surface 121 of the lateral side 102 of the covering 105. In some embodiments, the first tube guide 125 may generally form an S-shape. However, in other embodiments, the first tube guide 125 may form any shape so as to create the desired amount of tension around the wearer's foot and/or ankle region when adjusting the tightening mechanism 110. Both the first segment 115 and the first tube guide 125 may extend from the cable tightening mechanism 110 to the lateral side edge 170 adjacent to the top edge 174 of the covering 105.

As seen in FIG. 3, the first segment 115 may continue to extend in, and may be slidably engaged with, the second tube guide 140 located on the first surface 160 of the first fastener 106. Both the first segment 115 and the second tube guide 140 may extend along the first surface 160 of the first fastener 106 forming a U-shape. The first segment 115 may continue to extend beyond the second tube guide 140 and into the third tube guide 142 located along the lateral side edge 170 between the first fastener 106 and the second fastener 111. The first segment 115 may continue to extend in, and may be slidably engaged with, the third tube guide 142, forming a U-shape on the outer surface 121 of the covering 105 along the lateral side edge 170. The first segment 115 may continue to extend beyond the third tube guide 142 and into the fourth tube guide 144 located on the first surface 162 of the second fastener 111. The first segment 115 may continue to extend in, and may be slidably engaged with, the fourth tube guide 144 forming a U-shape on the first surface 162 of the second fastener 111. The first segment 115 may continue to extend beyond the fourth tube guide 144 and into the fifth tube guide 146 located on the bottom portion 178 of the covering 105. The first segment 115 may continue to extend in, and be slidably engaged with, the fifth tube guide 146. Both the first segment 115 and the fifth tube guide 146 may extend from the fourth tube guide 144 adjacent to the lateral side edge 170 down along the outer surface 154 of the bottom strap 150.

As the cable 117 extends through the fifth tube guide 146 along the outer surface 154 of the bottom strap 150, the cable 117 leaves the lateral side 102 and reaches the medial side 103 of the covering 105. At that point, the first segment 115 becomes the second segment 120 of the cable 117. Both the second segment 120 and the fifth tube guide 146 continues up the medial side 103 of the outer surface 154 of the bottom strap 150 towards the tightening mechanism 110. The second segment 120 of the cable then extends beyond the fifth tube guide 146 and may be associated with the cable tightening mechanism 110.

In some embodiments, the covering 105 may include provisions for a bottom strap 150 to secure around the sole 137 of the article of footwear 130. In some embodiments, the bottom strap 150 may include a medial bottom strap and a lateral bottom strap that may be attached to one another once the article of footwear 130 is inserted in the opening 156. However, in other embodiments, as shown in FIG. 3, a continuous bottom strap 150 may form an opening 156 for inserting at least a portion of the article of footwear 130. The bottom strap 150 may include a fifth tube guide 146 formed on the outer surface 154, and may have an inner surface 152 for contacting the outer surface of the article of footwear 130.

Figure 4:
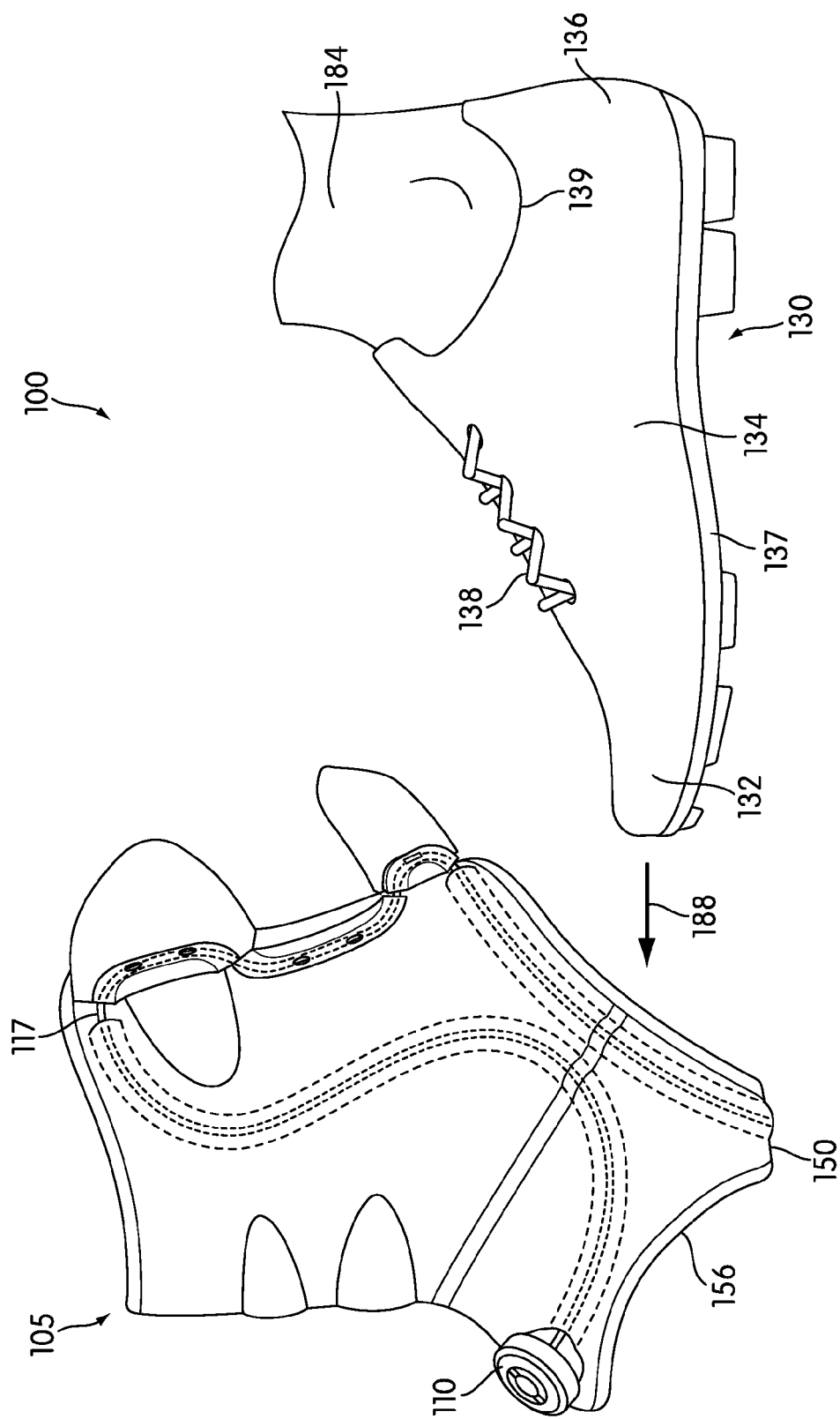
FIG. 4 is a lateral side view of an embodiment of a removable ankle support system as the foot is inserted into the covering.

FIGS. 4-7 show one embodiment of how an article of footwear 130 may be inserted into the covering 105 and how the covering 105 may be tightened and loosened using the cable tightening mechanism 110. FIG. 4 shows a lateral side 102 view of the ankle support system 100 with the covering 105 in an open condition as in FIG. 3. The wearer's foot 184 has been inserted into the collar 139 of the article of footwear 130, and is ready to receive the covering 105. The forefoot region 132 of the article of footwear 130 may then be moved in a first direction 188 through the opening 156 in the covering 105.

Although FIG. 4 shows the article of footwear 130 approaching the covering 105 through an opening formed between the lateral side edge 170 and the medial side edge 172 of the covering 105 in the back of the covering 105, other embodiments may include inserting the article of footwear 130 through an opening formed in the front of the covering 105. In other embodiments, the article of footwear 130 may be inserted into the covering 105 through an opening on either the lateral 102 or medial side 103 of the covering 105.

Figure 5:
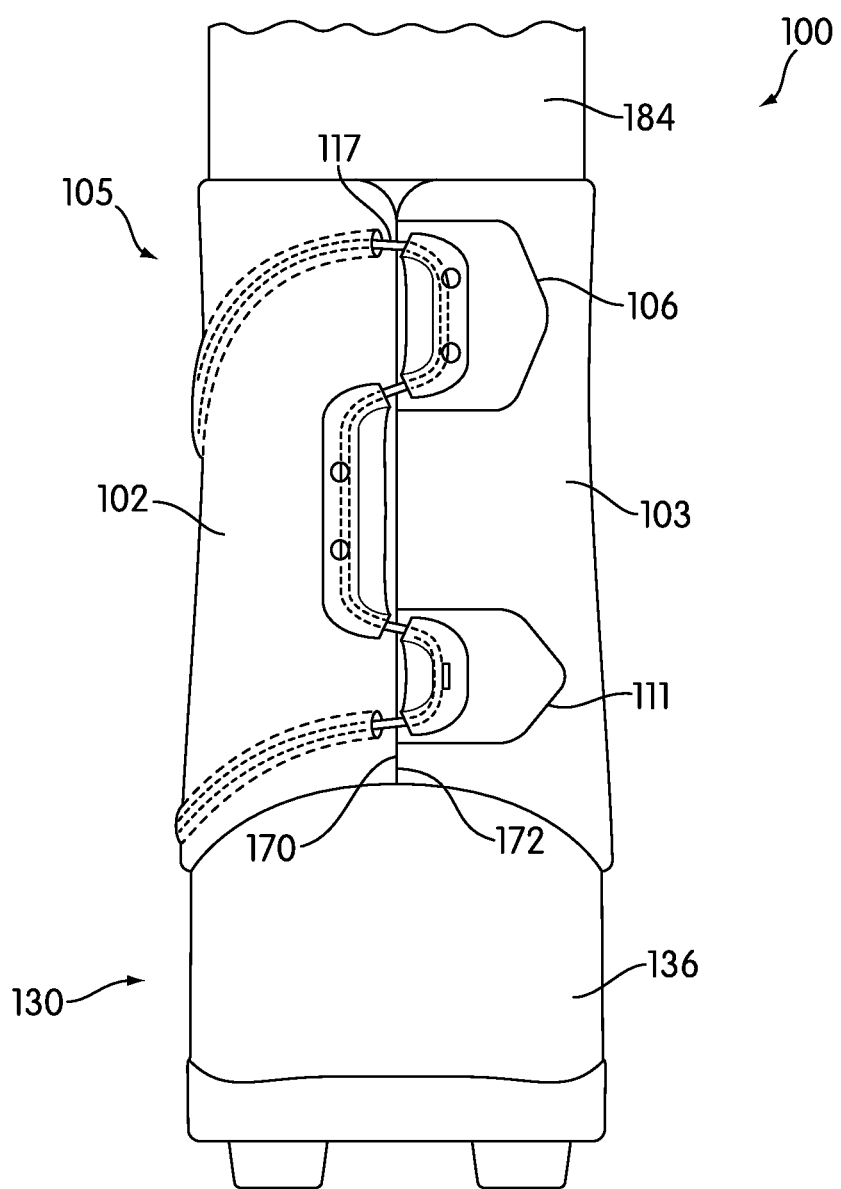
FIG. 5 is a rear view of an embodiment of an ankle support system where the first and second fasteners are secured once the foot is positioned in the covering.

FIG. 5 is a rear view of the covering 105 in a closed condition once the covering 105 has been positioned over a portion of the article of footwear 130. As can be seen in FIG. 5, the lateral side edge 170 of the covering 105 may be brought into close proximity with the medial side edge 172 of the covering 105. The first fastener 106 and second fastener 111, which may be hingedly attached to the lateral side 102 of the covering 105, may then be secured to the medial side 103 of the covering 105 by any of the methods discussed in FIGS. 1 and 3.

Figure 6:
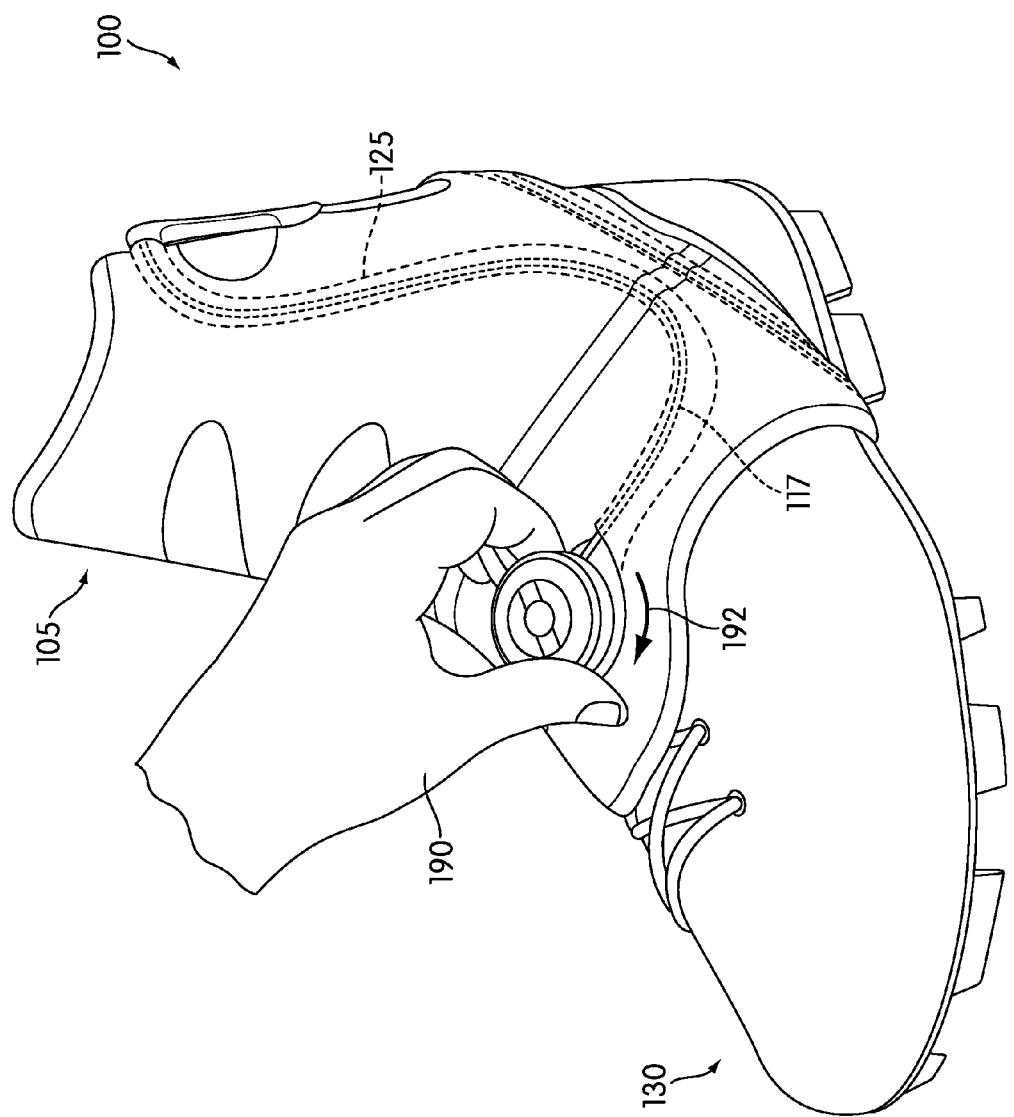
FIG. 6 is a perspective view of an embodiment of an ankle support system where tension is being applied to the cable using the cable tightening mechanism.

FIG. 6 shows a hand 190 turning the cable tightening mechanism 110 in a clockwise direction 192. Turning the cable tightening mechanism 110 may reduce the effective length of the cable 117 by winding the cable 117 around the cable tightening mechanism 110 as described above. When the slack is removed from cable 117, cable 117 may pull on the covering 105 since the cable 117 is slidably engaged with the covering 105. This pulling motion may cinch the covering 105 around the foot 184 of the wearer. In other embodiments, hand 190 may turn the cable tightening mechanism 110 in a counterclockwise direction in order to achieve the same effects as that described in FIG. 6.

Figure 7:
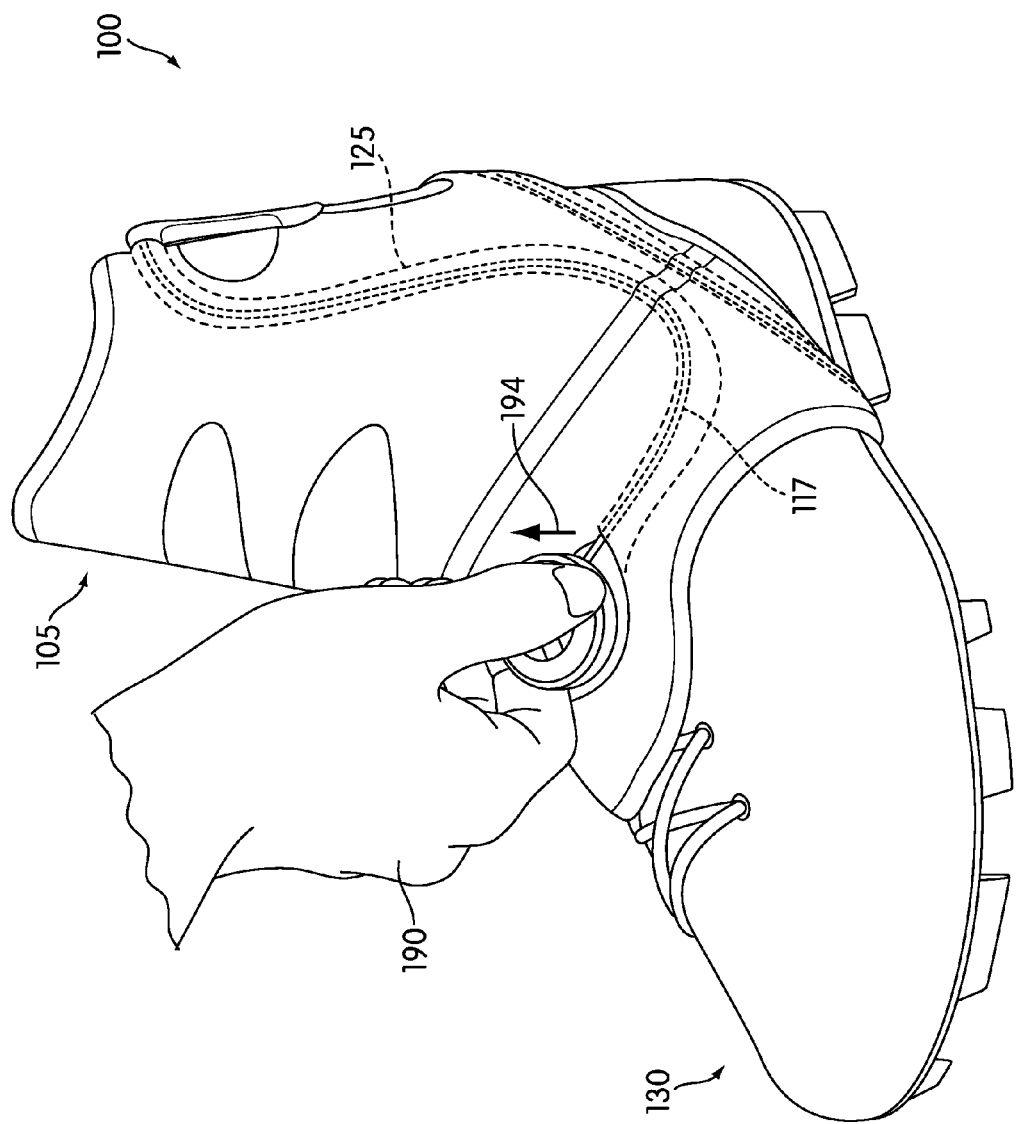
FIG. 7 is a perspective view of an embodiment of an ankle support system where tension is being released from the cable using the cable tightening mechanism.

FIG. 7 shows how cable 117 may be loosened. Hand 190 pulls on the cable tightening mechanism 110 in an outwardly direction 194 away from the covering 105. Pulling the cable tightening mechanism 110 in an outwardly direction 194 may cause the cable 117 to unwind. The effective length of the cable 117 may be lengthened and slack returns to the cable 117. This slack may allow the covering 105 to move away from the wearer's foot 184. Once the cable 117 has been loosened in this fashion, the covering 105 may be removed from the article of footwear 130.

Figure 8:
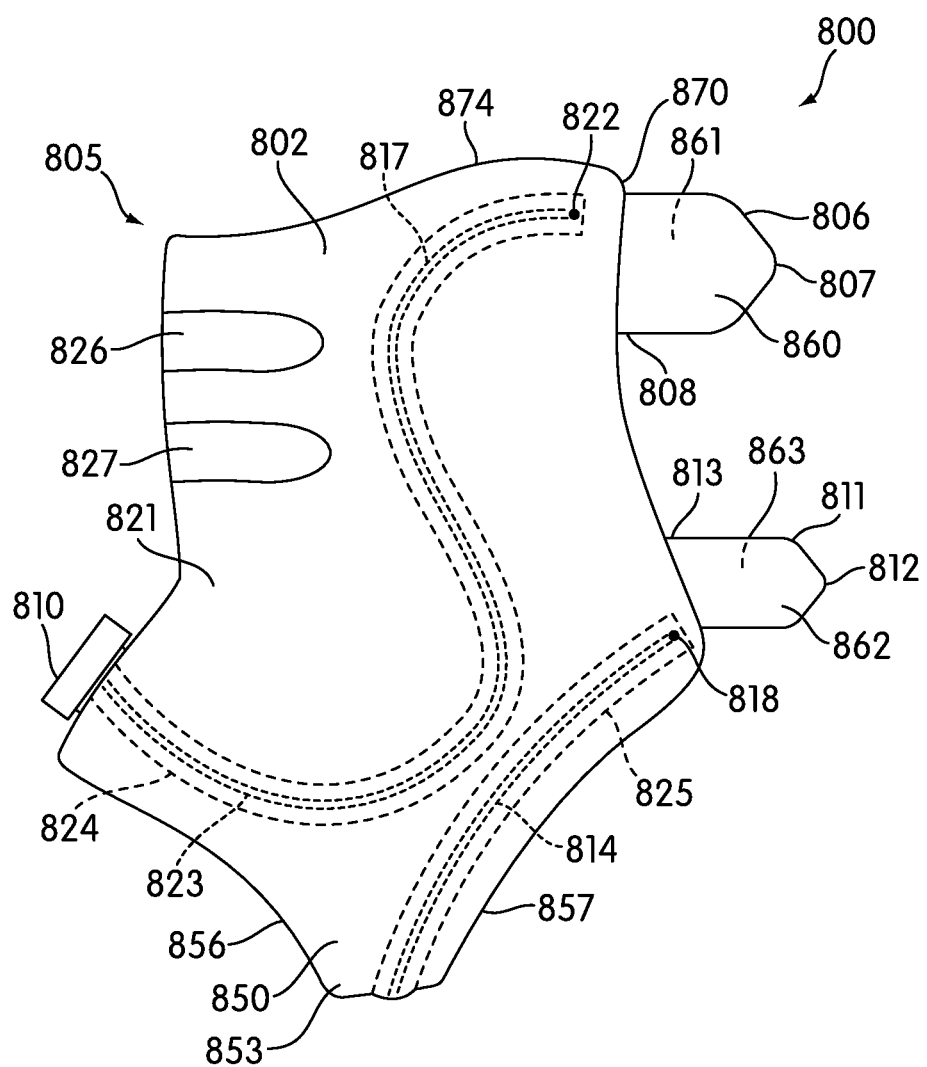
FIG. 8 is a lateral side view of another embodiment of a covering for use in an ankle support system.
Figure 9:
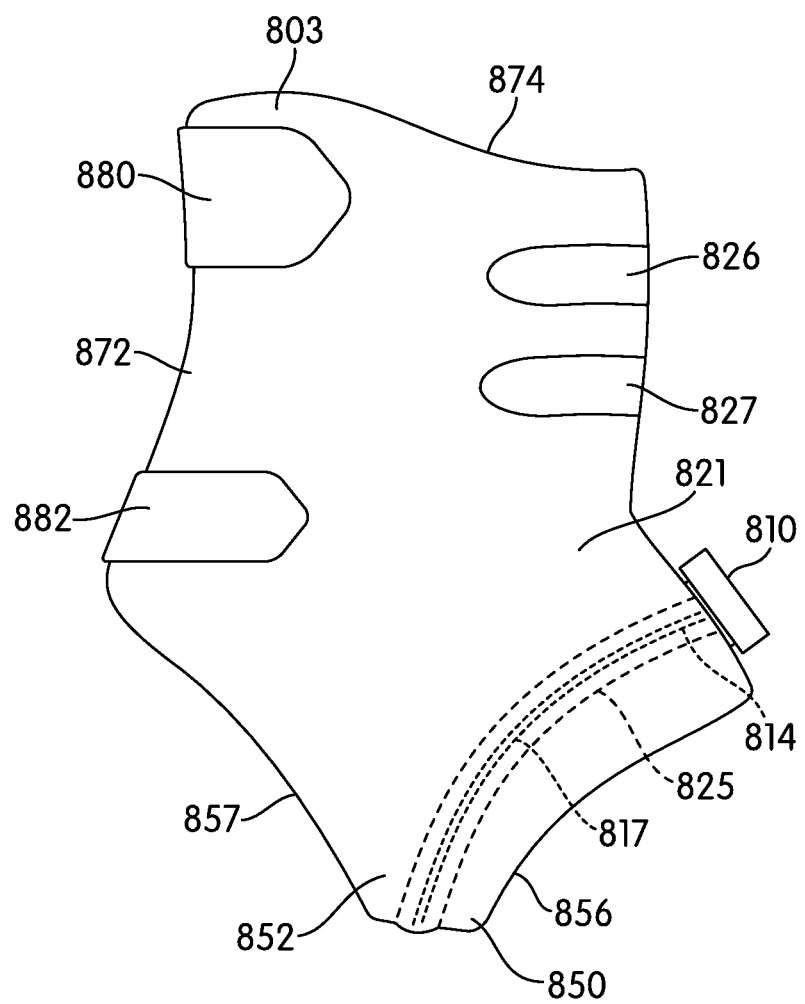
FIG. 9 is a medial side view of the covering shown in FIG. 8.

FIGS. 8-9 show a covering 805 in accordance with another embodiment of an ankle support system 800. FIG. 8 shows a lateral side 802 view of the covering 805, while FIG. 9 shows a medial side 803 view of the covering 805. Unlike the covering 105 discussed in FIGS. 1-7, where the cable 117 forms a closed loop that is slidably engaged with the covering 105, the ends of the cable 817 shown in FIGS. 8-9 may be secured to a surface or portion of the covering 805. Securing the ends of the cable 817 to a portion of the covering 805 allows the length of cable 817 to be shortened since the cable 817 may not extend into the first fastener 806 and second fastener 811 portions of the covering 805.

The covering 805 shown in FIGS. 8-9 may be made from the same materials, and may have a similar construction, as the materials and processes discussed for covering 105.

In some embodiments of an ankle support system 800, provisions may be provided for a covering 805 having different regions or zones of flexibility and/or rigidity. In some embodiments, the covering 805 may include one or more layers of material having different properties relating to rigidity and/or flexibility. In some embodiments, rigid material may be included in regions where additional support is desired. For example, some embodiments may include material made from carbon fibers and/or glass fibers in areas where more rigidity is desired. In other embodiments, rigid material may be excluded or minimized in areas or zones where more flexibility is desired. For example, some embodiments may include layers where rigid material has been cut out or removed from the regions or zones where a higher degree of flexibility is desired. In other embodiments, the thickness of the rigid material may be reduced in areas where more flexibility is desired.

In some embodiments of an ankle support system 800, ventilation may be provided throughout different areas, or zones, of the covering 805, in order to remove humidity trapped near the foot. In some embodiments, ventilation may be provided by holes, channels and/or cut out portions in one or more layers of the covering 805. In some embodiments, the holes, channels, or cut out portions that provide ventilation may also provide regions or zones of flexibility. However, in other embodiments, the regions providing ventilation may be separate from the regions that provide increased flexibility.

In some embodiments, as shown in FIGS. 8 and 9, the covering 805 may include a first cut out region 826 and a second cut out region 827. In some embodiments, the first cut out region 826 and/or second cut out region 827 may provide for ventilation allowing humidity trapped near the foot to escape. In some embodiments, the first cut out region 826 and/or second cut out region 827 may provide for a zone or region of increased flexibility. In some embodiments, the first cut out region 826 and/or second cut out region 827 may provide for ventilation in addition to a region of increased flexibility. Although the first cut out region 826 and second cut out region 827 are generally elongated in shape, the first cut out region 826 and second cut out region 827 may be any shape. For example, the first cut out region 826 and second cut out region 827 may generally be, but not limited to, circular, square, rectangular, or any other geometric shape. Although FIGS. 8-9 show a first cut out region 826 and second cut out region 827, other embodiments may include more or less cut out regions. Although the ankle support system 800 shown in FIGS. 8-9 includes two cut out regions, some embodiments may include more or less cut out regions.

In some embodiments of an ankle support system 800 provisions may be included for securing the covering 805 around a portion of an article of footwear. For example, some embodiments may include provisions for preventing the covering 805 from shifting or moving during athletic activity. In some embodiments, the covering 805 may include one or more components that hold the covering 805 securely in place in a variety of different manners. In some embodiments, fasteners or straps may be used to securely position the covering 805. In some embodiments, clasps, buttons, snaps, buckles, hooks, adhesives, or other structure known in the art may be used to securely the position the covering 805 in place. In some embodiments, fastener portions may be held in place by hook and loop fasteners (such as Velcro) located on a surface of the fastener portion, as well as surfaces that receive the fastener portions.

FIG. 8 shows a first fastener 806 for securing the covering 805 in place. Referring to FIG. 8, the first fastener 806 may be located on the lateral side 802 of the covering 805, and may be adjacent to the lateral side edge 870 of the covering 805. The first fastener 806 may include a first end 807 that is distal to the lateral side edge 870 and a second end 808 that is proximate to the lateral side edge 870. In some embodiments, the second end 808 is hingedly attached to the lateral side edge 870 by any manner known in the art. For example, the second end 808 may be sewn, affixed, adhered, snapped, buckled and/or fastened to the lateral side edge 870. The first fastener 806 may include a first surface 860 and a second surface 861. In some embodiments, the second surface 861 may include hook and loop fasteners (such as Velcro). In other embodiments, the first surface 860 may include hook and loop fasteners (such as Velcro).

Referring to FIG. 9, some embodiments may include a first fastener receiving portion 880 that may be adapted to receive the second surface 861 or first surface 860 of the first fastener 806. In some embodiments, a first fastener receiving portion 880 may be located on the medial side 803 of the covering 805, and may be adjacent to the medial side edge 872 of the covering 805. In some embodiments, the second surface 861 of the first fastener 806 and the first fastener receiving portion 880 may include hook and loop fasteners (such as Velcro). However, first fastener receiving portion 880 may be adapted to receive the second surface 861 of the first fastener 806 in any manner known in the art.

In addition to the first fastener 806, the covering may also include a second fastener 811. Referring to FIG. 8, some embodiments may include a second fastener 811 located on the lateral side 802 of the covering 805, and may be adjacent to the lateral side edge 870 of the covering 805. The second fastener 811 may include a first end 812 that is distal to the lateral side edge 870 and a second end 813 that is proximate to the lateral side edge 870. In some embodiments, the second end 813 is hingedly attached to the lateral side edge 870 by any manner known in the art. For example, the second end 813 may be sewn, affixed, adhered, snapped, buckled and/or fastened to the lateral side edge 870. The second fastener 811 may include a first surface 862 and a second surface 863. In some embodiments, the second surface 863 may include hook and loop fasteners (such as Velcro). In other embodiments, the first surface 862 may include hook and loop fasteners (such as Velcro).

In some embodiments, a second fastener receiving portion 882 may be adapted to receive the second surface 863 or first surface 862 of the second fastener 811. Referring to FIG. 9, a second fastener receiving portion 882 may be located on the medial side 803 of the covering 805, and may be adjacent to the medial side edge 872 of the covering 805. In some embodiments, the second fastener receiving portion 882 may include hook and loop fasteners (such as Velcro). However, second fastener receiving portion 882 may be adapted to receive the second surface 863 of the second fastener 811 in any manner known in the art. Although FIGS. 8 and 9 describe a covering 805 having two fasteners and two fastener receiving portions, other embodiments may include more or less fasteners and/or fastener receiving portions.

Some embodiments of an ankle support system 800 may include provisions for adjusting the tightness of the covering 805 once the covering 805 has been arranged into a closed condition around the article of footwear. In some embodiments, a cable 817 may be slidably engaged with the covering 805 and may be tightened using a tightening mechanism 810 in order to adjust the desired tension. The cable 817 may be made of any material known in the art, such as metals, textiles, fiber components, or the like. The cable 817 may have any size or shape known in the art, for example, a single filament, separate filaments bound or braided together, or may include a flat ribbon of material.

The cable tightening mechanism 810 in some embodiments may vary. In some embodiments, the cable tightening mechanism 810 shown in FIG. 8 may have similar properties and characteristics as the cable tightening mechanism 110 described in FIGS. 1-7. However, as will be discussed in FIGS. 21-23, the cable tightening mechanism 810 may also include a removable cam lever system. In some embodiments, the cable tightening mechanism 810 may be associated with the cable 817 in the same manner as the cable tightening mechanism 110 associates with cable 117 in FIGS. 1-7.

Unlike the cable 117 described in FIGS. 1-7, the cable 817 described in FIGS. 8-9 may not form a continuous loop. Instead, a first free end 822 and a second free end 818 of the cable 817 may be attached to any surface of the covering 805. In some embodiments, as shown in FIG. 8, the first free end 822 of cable 817 may be attached to an outer surface 821 on the lateral side 802 of covering 805. The portion of the cable 817 extending between the first free end 822 and the cable tightening mechanism 810 may form a first cable segment 823. The first cable segment 823 may extend in, and be slidably engaged with, a first tube guide 824 attached to the outer surface 821 of the covering 805. Both the first cable segment 823 and the first tube guide 824 may extend from the top edge 874 of the covering 805 near the lateral side edge 870 down to the cable tightening mechanism, forming an S-shape on the lateral side 802 of the covering 805. Although first cable segment 823 and first tube guide 824 forms an S-shape, the first cable segment 823 and first tube guide 824 may form any pattern on the covering 805 so that a sufficient amount of support is provided to the wearer's ankle and foot.

The cable 817 may continue to extend beyond the first tube guide 824, and may be associated with the cable tightening mechanism 810. In some embodiments, a portion of the cable 817 may be wound around the cable tightening mechanism 810 and continue to extend along the medial side 803 of the covering 805, as shown in FIG. 9. Referring to FIG. 9 the portion of the cable 817 extending from the cable tightening mechanism 810 along the medial side 803 of the covering 805 may form a second cable segment 814. The second cable segment 814 may extend in, and be slidably engaged with, a second tube guide 825. Both the second cable segment 814 and second tube guide 825 may extend from the cable tightening mechanism 810 along the medial bottom portion 852 of bottom strap 850, continuing up along the lateral portion 853 of bottom strap 850 to the second free end 818 adjacent to the lateral side edge 870 and the second fastener 811, as shown in FIG. 8. In some embodiments, the second free end 818 of the cable 817 may be attached to the outer surface 821 of the covering 805.

The ankle support system 800 operates similar to the ankle support system 100 discussed in FIGS. 1-7. For example, in some embodiments, the ankle support system 800 may include an article of footwear (not shown in FIGS. 8-9). In one embodiment, the forefoot of the article of footwear may be positioned through the back opening 857, until the forefoot portion is extending through the front opening 856 in the covering 805. Other aspects relating to donning and doffing the covering 805, are similar to donning and doffing the covering 805 discussed in FIGS. 1-7. Similarly, the methods of tightening and loosening the cables in the ankle support system 800 are similar those discussed in the ankle support system 100 discussed in FIGS. 1-7.

Figure 10:
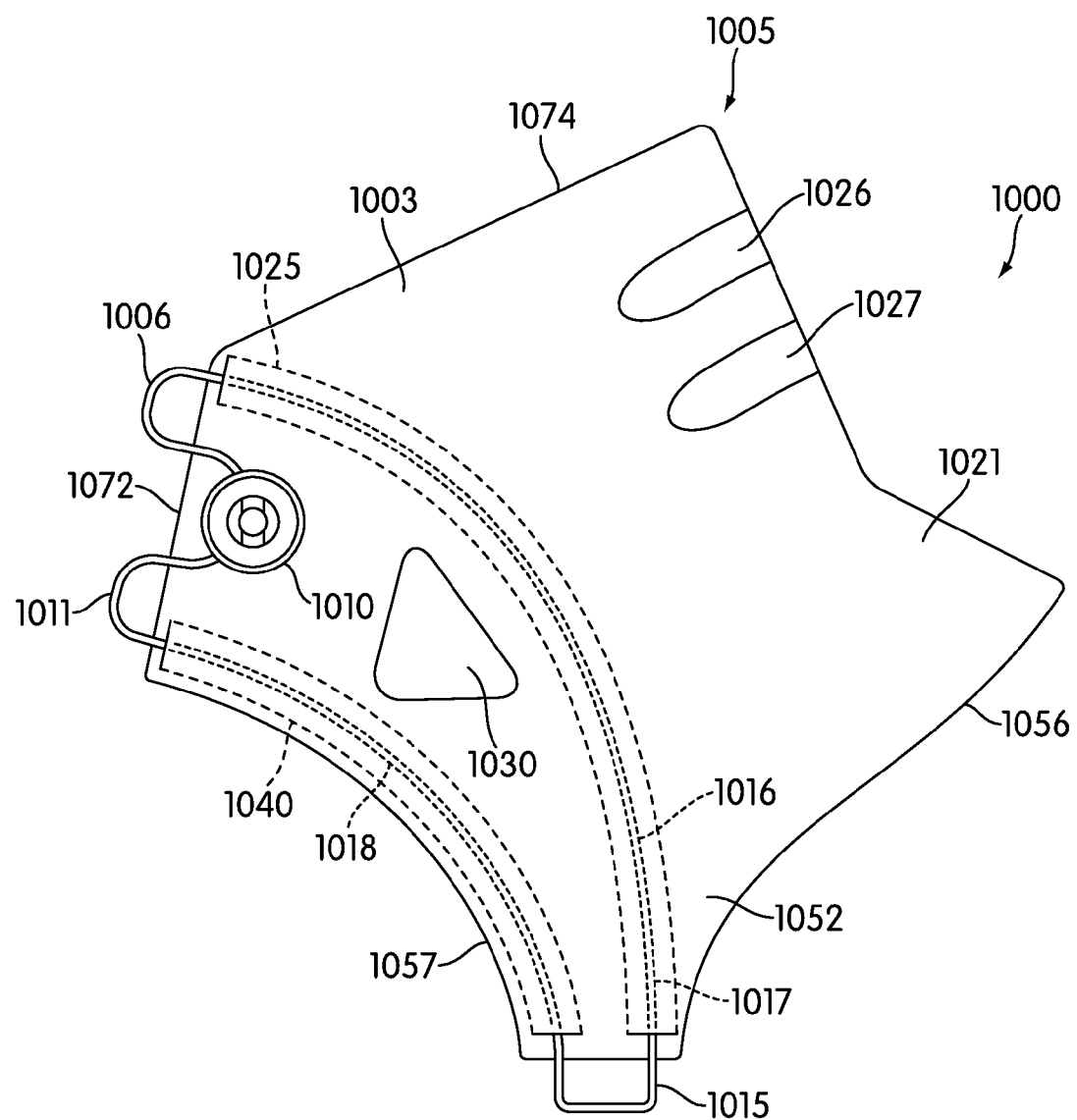
FIG. 10 is a medial side view of another embodiment of a covering for use in an ankle support system.
Figure 11:
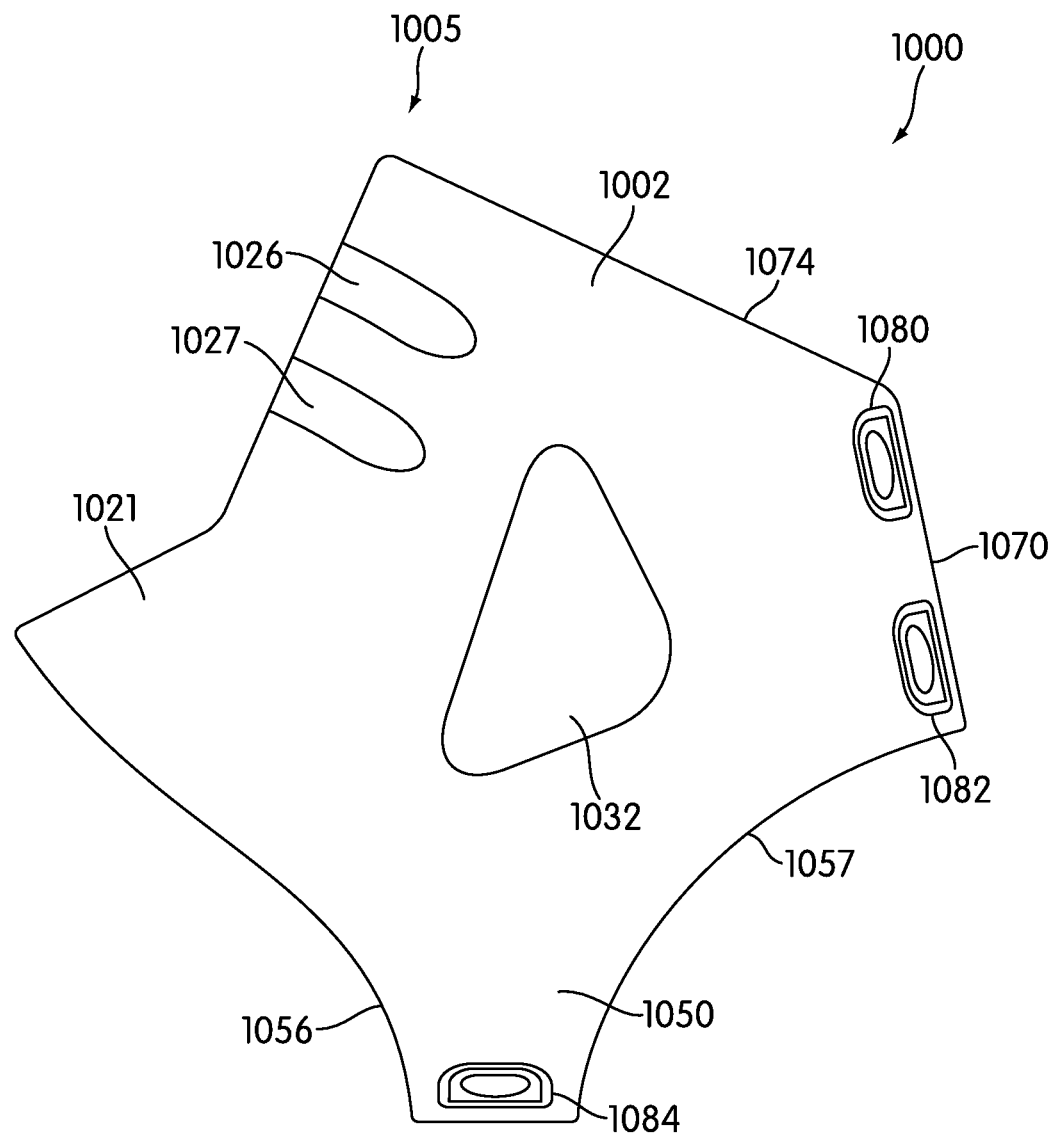
FIG. 11 is a lateral side view of the covering shown in FIG. 10.

FIGS. 10-11 show a covering 1005 in accordance with another embodiment of an ankle support system 1000. FIG. 10 shows a medial side 1003 view of the covering 1005, while FIG. 11 shows a lateral side 1002 view of the covering 1005. Unlike the cable 817 having free ends which are secured to the covering 805 as discussed in FIGS. 8-9, the cable 1017 in FIGS. 10-11 may form a closed loop that is slidably engaged with the covering 1005. In addition, unlike the covering 805 in FIGS. 8-9 having a first fastener 806 and a second fastener 811, the covering 1005 in FIGS. 10-11 has a first exposed cable loop 1006 and second exposed cable loop 1011. Unlike the covering 805 having a bottom strap 850 extending around the sole of the article of footwear in FIGS. 8-9, the covering 1005 in FIGS. 10-11 has a third exposed cable loop 1015. The exposed cable loops may be secured around loop receiving members located on the surface of the covering 1005, instead of the Velcro fasteners discussed in FIGS. 8-9. Other differences and similarities between the embodiments in FIGS. 10-11 and other embodiments disclosed herein are discussed below.

The covering 1005 shown in FIGS. 10-11 may be made from the same materials, and may have a similar construction, as the materials and processes discussed for covering 105.

In some embodiments, the covering 1005 includes a first cut out region 1026 and a second cut out region 1027. The first cut out region 1026 and second cut out region 1027 are similar to the first cut out region 126 and second cut out region 127 discussed in FIGS. 1-7. In some embodiments, as shown in FIG. 10, the ankle support system 1005 may also include a third cut out region 1030 on the medial side 1003 of the covering 1005. In some embodiments, as shown in FIG. 11, a fourth cut out region 1032 may be located on the lateral side 1002 of the covering 1005. The third cut out region 1030 and fourth cut out region 1032 are similar in nature and purpose as the first cut out region 126 and second cut out region 127. Although the third cut out region 1030 and fourth cut out region 1032 are generally triangular in shape, the third cut out region 1030 and fourth cut out region 1032 may be any shape. For example, the third cut out region 1030 and fourth cut out region 1032 may generally be, but not limited to, circular, square, rectangular, or any other geometric shape. Although the embodiment shown in FIGS. 10-11 includes a total of four cut out regions, other embodiments may include more or less cut out regions.

In some embodiments of an ankle support system 1000, provisions may be included for securing the covering 1005 around a portion of an article of footwear. For example, some embodiments may include provisions for preventing the covering 1005 from shifting or moving during athletic activity. In some embodiments, the covering 1005 may include one or more components that hold the covering 1005 securely in place in a variety of different manners. In some embodiments, fasteners or straps may be used to securely position the covering 1005. In some embodiments, clasps, buttons, snaps, buckles, hooks, adhesives, or other structure known in the art may be used to securely the position the covering 1005 in place. In some embodiments, fastener portions may be held in place by hook and loop fasteners (such as Velcro) located on a surface of the fastener portion, as well as surfaces that receive the fastener portions. In some embodiments, exposed loops of cable may be fastened around loop receiving portions mounted on the surface of the covering 1005.

FIG. 10 shows one embodiment of a closed loop of cable 1016 that is slidably engaged with a covering 1005. In some embodiments, portions of the cable 1016 may form one or more exposed cable loops that may extend from the covering 1005. In some embodiments, a first exposed cable loop 1006 may extend from between the cable tightening mechanism 1010 and the first tube guide 1025. Referring to FIG. 10, the first exposed cable loop 1006 may be located on the medial side 1003 of the covering 1005, and may be adjacent to the medial side edge 1072 of the covering 1005. The cable 1016 may extend beyond the first exposed cable loop 1006 and into a first tube guide 1025 forming a first cable segment 1017. The first cable segment 1017 may extend in, and be slidably engaged with, the first tube guide 1025. Both the first cable segment 1017 and the first tube guide 1025 may extend from the first exposed cable loop 1006 down to the medial bottom strap 1052.

In some embodiments, a second exposed cable loop 1011 may extend from between the cable tightening mechanism 1010 and the second tube guide 1040. Referring to FIG. 10, the second exposed cable loop 1011 may be located on the medial side 1003 of the covering 1005, and may be adjacent to the medial side edge 1072 of the covering 1005. The cable 1016 may extend beyond the second exposed cable loop 1011 and into a second tube guide 1040. The portion of the cable 1016 extending in the second tube guide 1040 may form a second cable segment 1018. The second cable segment 1018 may extend in, and be slidably engaged with, the second tube guide 1040. Both the second cable segment 1018 and the second tube guide 1040 may extend from the second exposed cable loop 1011 along the back edge 1057 and down to the medial bottom strap 1052.

In some embodiments, a third exposed cable loop 1015 may extend from the medial bottom strap 1052. The third exposed cable loop 1015 may extend between the first tube guide 1025 and the second tube guide 1040. Although FIGS. 10-11 disclose a covering 1005 having three exposed cable loops, other embodiments may have more or less exposed cable loops.

Referring to FIG. 11, some embodiments may include a first loop receiving member 1080 that may be adapted to receive the first exposed cable loop 1006. In some embodiments, a loop receiving member 1080 may be located on the lateral side 1002 of the covering 1005, and may be adjacent to the lateral side edge 1070 and the top edge 1074 of the covering 1005.

In some embodiments, a second loop receiving member 1082 may be adapted to receive the second exposed cable loop 1011. Referring to FIG. 11, a second loop receiving member 1082 may be located on the lateral side 1002 of the covering 1005, and may be adjacent to the lateral side edge 1070 and the back edge 1057 of the covering 1005.

In some embodiments, a third loop receiving member 1084 may be adapted to receive the third exposed cable loop 1015. A third loop receiving member 1084 may be located on the lateral side 1002 of the covering 1005, and may be located on the lateral bottom strap 1050. The first loop receiving member 1080, second loop receiving member 1082 and third loop receiving member 1084 will be discussed in more detail in FIGS. 12-13.

Some embodiments of an ankle support system 1000 may include provisions for adjusting the tightness of the covering 1005 once the covering 1005 has been arranged into a closed condition around the article of footwear. In some embodiments, a cable 1016 may be slidably engaged with the covering 1005 and may be tightened using a tightening mechanism 1010 in order to adjust the desired tension. The cable 1016 may be made of any material known in the art, such as metals, textiles, fiber components, or the like. The cable 1016 may have any size or shape known in the art, for example, a single filament, separate filaments bound or braided together, or may include a flat ribbon of material.

The cable tightening mechanism 1010 in some embodiments may vary. In some embodiments, the cable tightening mechanism 1010 shown in FIG. 10 may have similar properties and characteristics as the cable tightening mechanism 110 described in FIGS. 1-7. However, as will be discussed in FIGS. 21-23, the cable tightening mechanism 1010 may also include a removable cam lever system. In some embodiments, the cable tightening mechanism 1010 may be associated with the cable 1016 in the same manner as the cable tightening mechanism 110 associates with cable 117 in FIGS. 1-7.

The ankle support system 1000 shown in FIGS. 10-11 operates similar to the ankle support system 100 discussed in FIGS. 1-7. For example, in some embodiments, the ankle support system 1000 may include an article of footwear (not shown in FIGS. 10-11). In one embodiment, the forefoot of the article of footwear may be positioned through the back edge 1057, until the forefoot portion is extending through the front opening 1056 in the covering 1005. Other aspects relating to donning and doffing the covering 1005, are similar to donning and doffing the covering 105 discussed in FIGS. 1-7. Similarly, the methods of tightening and loosening the cables in the ankle support system 1000 are similar to those discussed in the ankle support system 100 discussed in FIGS. 1-7.

Some embodiments of an ankle support system may include provisions for fastening or securing a covering around an article of footwear. Some embodiments, as discussed in FIGS. 10-11, may include exposed portions of cable that form loops which may then be positioned around a loop receiving member that is attached to the covering and/or an article of footwear.

Figure 12:
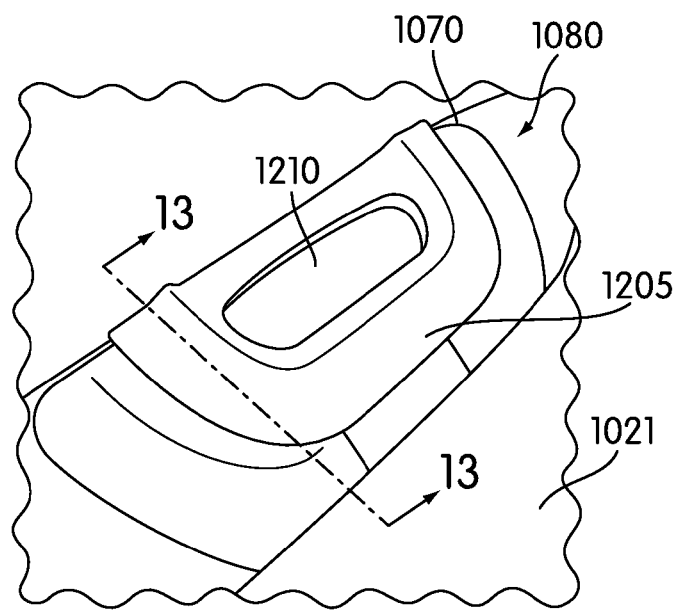
FIG. 12 is one embodiment of a loop receiving member for use in an ankle support system.
Figure 13:
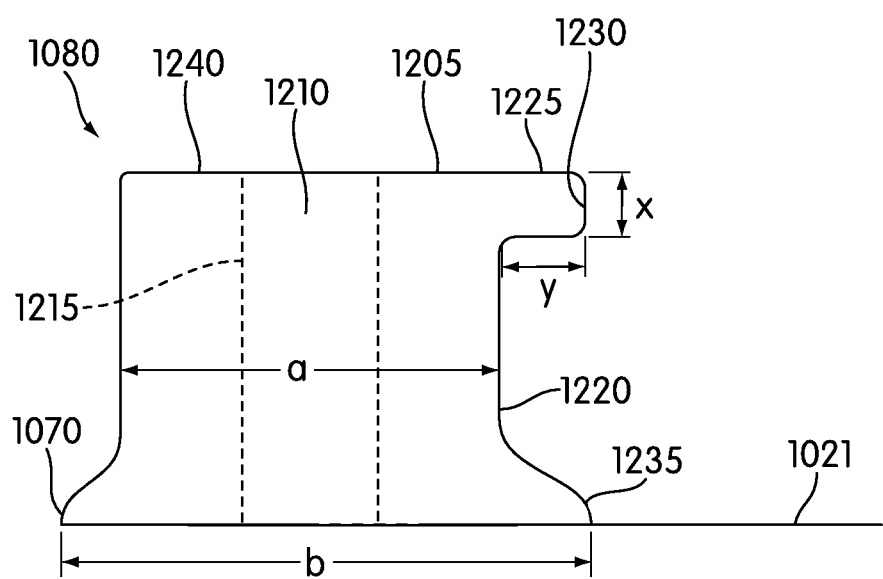
FIG. 13 is an enlarged cross-sectional side view of the loop receiving member shown in FIG. 12.

FIGS. 12-13 shows one embodiment of a first loop receiving member 1080, as discussed in FIG. 11. Although FIGS. 12-13 are directed towards a first loop receiving member 1080, any loop receiving member discussed herein may have a similar structure to the embodiment shown in FIGS. 12-13. For example, second loop receiving member 1082 and third loop receiving member 1084 may have similar structures and properties as the embodiment discussed in FIGS. 12-13.

Some embodiments of a loop receiving member may include a structure extending outwardly from an outer surface of a covering and/or an article of footwear. In some embodiments, the diameter of the distal end of the loop receiving member may be larger than the diameter of other portions of the loop receiving member. A loop receiving member having a larger diameter at the distal end assists in retaining the cable around the loop receiving member. Additionally, the proximate end of the loop receiving member may also have a larger diameter than other portions of the loop receiving member. A loop receiving member having a larger diameter at the proximal end raises the cable away from the outer surface of the covering and/or article of footwear and helps to reduce wear caused by friction between the cable and the covering and/or article of footwear.

In some embodiments, the structure of a loop receiving member may vary. In some embodiments, the structure of a loop receiving member may be any structure that sufficiently retains the cable around the loop receiving member during moderate and/or strenuous activities. In some embodiments, the loop receiving member may be hingedly attached to the surface of the covering and/or article of footwear. In other embodiments, the loop receiving member may be rigidly attached to the surface of the covering and/or article of footwear. In still further embodiments, the loop receiving member may be releasably attached to the surface of the covering and/or article of footwear. The shape of the loop receiving member in some embodiments may vary. In some embodiments, the loop receiving member may be circular, triangular, rectangular, square, oval, or any other geometric shape. In some embodiments, the loop receiving member may include a bracket, ring, or a D-ring.

Referring to FIG. 12, some embodiments may include a first loop receiving member 1080 positioned near a lateral side edge 1070 of the covering 1005. In some embodiments, the first loop receiving member 1080 may extend outwardly from the outer surface 1021 of the covering 1005. The top surface 1205 of the first loop receiving member 1080 may be substantially parallel to the outer surface 1021 of the covering 1005. However, in other embodiments, the top surface 1205 of the first loop receiving member 1080 may form some angle with the outer surface 1021 of the covering 1005.

In an exemplary embodiment, the top surface 1205 of the loop receiving member 1080 may be associated with a generally rounded rectangular shape. As shown in this embodiment, the top surface 1205 of the first loop receiving member 1080 may include a first curved portion on one end that extends from lateral side edge 1070 in an approximately perpendicular direction towards outer surface 1021 of the covering 1005. The top surface 1205 may also include a second curved portion on an opposite end that extends from outer surface 1021 in an approximately perpendicular direction towards lateral side edge 1070. The generally rounded rectangular shape may further be defined by an elongated central portion extending along the top surface 1205 facing towards outer surface 1021 of the covering 1005 in a generally parallel direction with lateral side edge 1070 and extending between the first curved portion and the second curved portion. In other embodiments, the top surface 1205 of the loop receiving member 1080 may be circular, triangular, rectangular, square, oval, or any other geometric shape. In various embodiments, one or more of the loop receiving members disposed on the covering and/or article of footwear may have a similar or different shape.

FIG. 13 shows a cross-sectional view of the first loop receiving member 1080 shown in FIG. 12. In some embodiments, the first loop receiving member 1080 may include an inner side surface 1215 forming an inner cavity 1210. In some embodiments, the distal end 1240 of the first loop receiving member 1080 may have a diameter that is larger than other portions of the first loop receiving member 1080.

As can be seen in FIG. 13, the mid portion 1220 of the first loop receiving member 1080 has a diameter a. The distal end 1240 of the first loop receiving member 1080 includes an outlaying portion 1225 that extends a distance y beyond diameter a of mid portion 1220. Outlaying portion 1225 also includes a side surface 1230 having a thickness x. The outlaying portion 1225 may assist in maintaining a cable loop within the mid portion 1220 of the first loop receiving member 1080 while the ankle support system 1000 is being worn.

In some embodiments, the proximal end 1235 of the first loop receiving member 1080 may have a diameter that is larger than other portions of the first loop receiving member 1080. As can be seen in FIG. 13, the proximate end 1235 of the loop receiving member 1080 has a diameter b, which is larger than diameter a of the mid portion 1220. The larger diameter at the proximate end 1235 may assist in lifting the cable loop away from the outer surface 1021 of the covering 1005 in order to minimize frictional wearing. In some embodiments, diameter b is equal to diameter a plus distance y. However, in other embodiments, diameter b is less than diameter a plus distance y. In still further embodiments, diameter b is greater than diameter a plus distance y.

FIGS. 14-18 show another embodiment of an ankle support system 1500. In the embodiment disclosed in FIGS. 14-18, the cable 1516 may form a closed loop that is slidably engaged with the covering 1505. In addition, the covering 1505 may have a first exposed cable loop 1523, a second exposed cable loop 1506, a third exposed cable loop 1515, and a fourth exposed cable loop 1511. The exposed cable loops may be secured around loop receiving members located on a surface of the covering 1505 and/or the article of footwear 1534, as well as one or more footwear loop anchors located on a surface of the upper of the article of footwear 1534. Other differences and similarities between the embodiments in FIGS. 14-18 and other embodiments disclosed herein are discussed below.

The covering 1505 shown in FIGS. 14-18 may be made from the same materials, and may have a similar construction, as the materials and processes discussed for covering 105 in FIGS. 1-7.

In some embodiments, the covering 1505 may include one or more cut out regions. For example, the covering 1505 may include a first cut out region 1526, a second cut out region 1527, a third cut out region 1528, a fourth cut out region 1529, a fifth cut out region 1530 and a sixth cut out region 1531. The first cut out region 1526, second cut out region 1527, third cut out region 1528, fourth cut out region 1529, fifth cut out region 1530 and sixth cut out region 1531 are similar in nature and purpose to the first cut out region 126 and second cut out region 127 discussed in FIGS. 1-7. In some embodiments, other cut out regions may be included on the outer surface 1521 of the covering 1505. Although the first cut out region 1526, second cut out region 1527, third cut out region 1528, fourth cut out region 1529, fifth cut out region 1530 and sixth cut out region 1531 are generally oval in shape, cut out regions may form any shape. For example, the first cut out region 1526, second cut out region 1527, third cut out region 1528, fourth cut out region 1529, fifth cut out region 1530 and sixth cut out region 1531 may generally be, but not limited to, circular, square, rectangular, or any other geometric shape. Although the embodiment in FIGS. 14-18 includes a total of six cut out regions, other embodiments may include more or less than six cut out regions.

In some embodiments of an ankle support system 1500, provisions may be included for securing the covering 1505 around a portion of an article of footwear 1534. For example, some embodiments may include provisions for preventing the covering 1505 from shifting or moving during athletic activity. In some embodiments, the covering 1505 may include one or more components that hold the covering 1505 securely in place in a variety of different manners. In some embodiments, fasteners or straps may be used to securely position the covering 1505. In some embodiments, clasps, buttons, snaps, buckles, hooks, adhesives, or other structure known in the art may be used to securely the position the covering 1505 in place. In some embodiments, fastener portions may be held in place by hook and loop fasteners (such as Velcro) located on a surface of the fastener portion, as well as surfaces that receive the fastener portions. In some embodiments, exposed loops of cable may be fastened around loop receiving members mounted on the surface of the covering 1505 and/or athletic footwear 1534.

Figure 14:
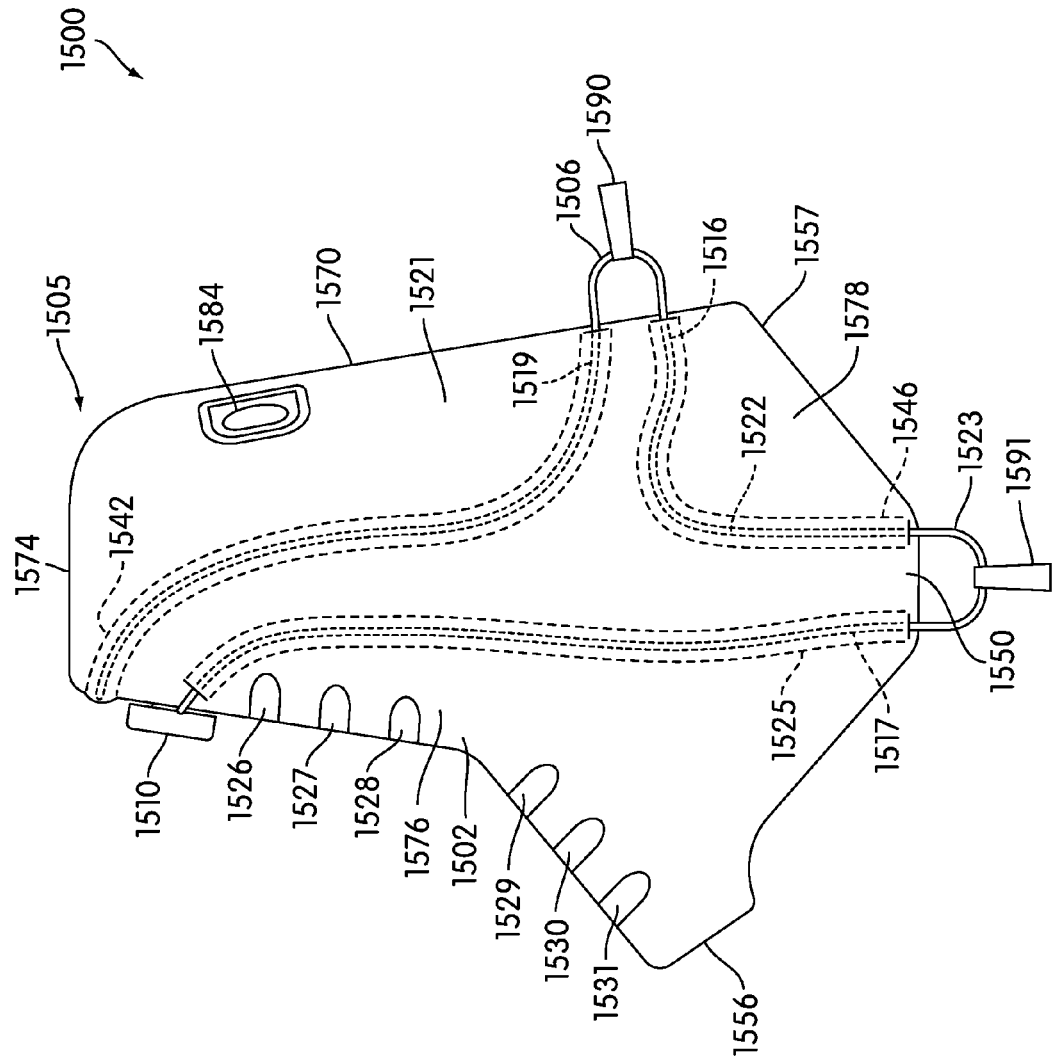
FIG. 14 is a lateral side view of another embodiment of a covering for use in an ankle support system.

In the embodiment shown in FIGS. 14-18, a closed loop of cable 1516 may be slidably engaged with covering 1505. In some embodiments, a first cable segment 1517 may be slidably engaged with a first tube guide 1525 attached to the outer surface 1521 of the covering 1505. As shown in FIG. 14, both the first cable segment 1517 and first tube guide 1525 extend between the cable tightening mechanism 1510 and the lateral bottom strap 1550 located at the bottom portion 1578 of the covering 1505. A second cable segment 1522 may be slidably engaged with a second tube guide 1546 attached to the outer surface 1521 of the covering 1525. Both the second cable segment 1522 and the second tube guide 1546 may extend from the lateral bottom strap 1550 to the lateral side edge 1570 in the bottom portion 1578 of the covering 1505. In some embodiments, a first exposed loop portion 1523 may extend from the lateral bottom strap 1550 between the first cable segment 1517 and the second cable segment 1522.

Figure 15:
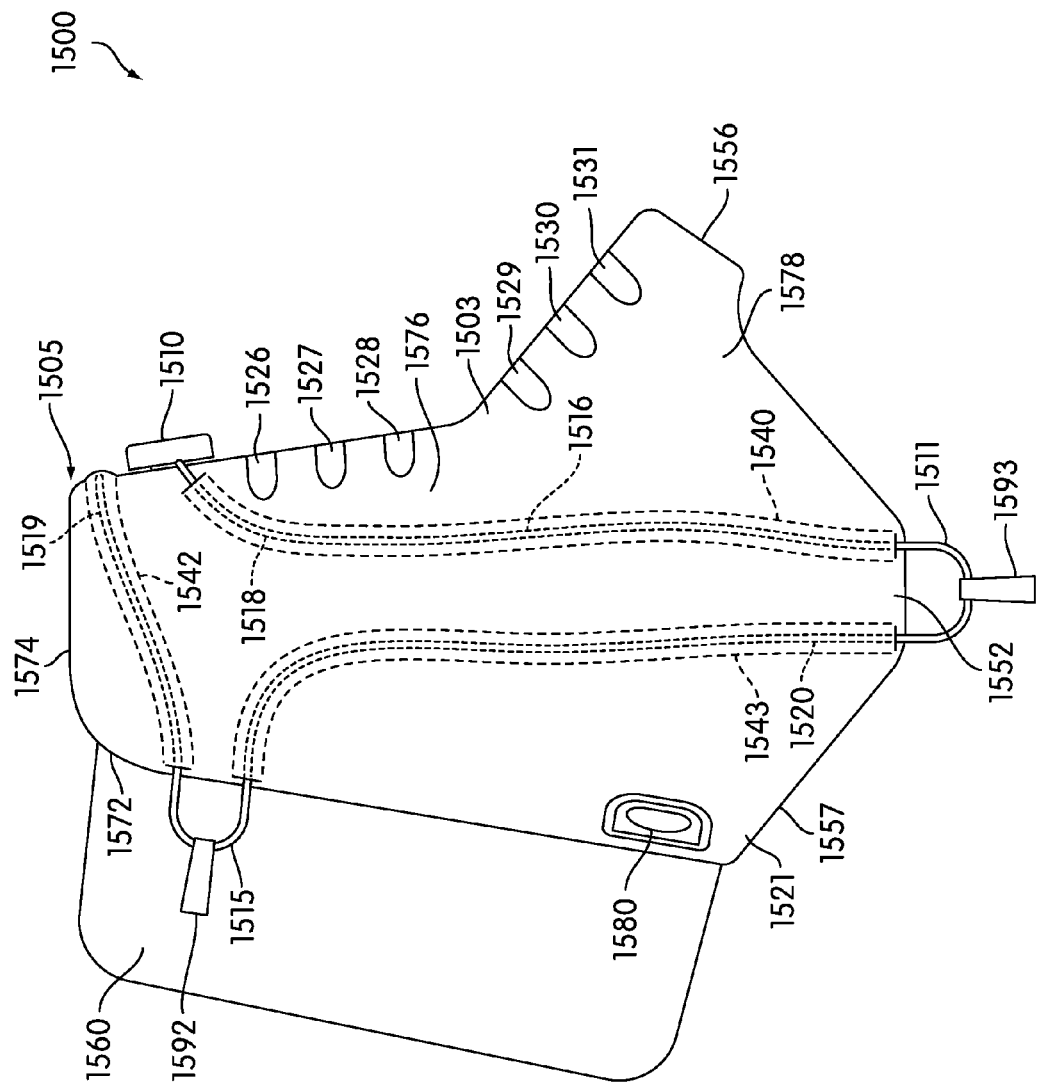
FIG. 15 is a medial side view of the covering shown in FIG. 14.

In some embodiments, a third cable segment 1519 may be slidably engaged with a third tube guide 1542 attached to the outer surface 1521 of the covering 1505. Both the third cable segment 1519 and the third tube guide 1542 may extend from the lateral side edge 1570 of the covering 1505, across the lateral side 1502, continuing above the cable tightening mechanism 1510 to the medial side 1503, and extending to the medial side edge 1572 adjacent the top edge 1574 of the covering 1505 as seen in FIG. 15. In some embodiments, a second exposed loop portion 1506 may extend from the lateral side edge 1570 between the second cable segment 1522 and the third cable segment 1519.

Referring to FIG. 15, some embodiments may include a fourth cable segment 1520 that may be slidably engaged with a fourth tube guide 1543 attached to the outer surface 1521 of the covering 1505. Both the fourth cable segment 1520 and the fourth tube guide 1543 may extend from the lateral side edge 1570 down to the medial bottom strap 1552. In some embodiments, a third exposed loop portion 1515 may extend from the medial side edge 1572 between the third cable segment 1519 and the fourth cable segment 1520.

In some embodiments, a fifth cable segment 1518 may be slidably engaged with a fifth tube guide 1540 attached to the outer surface 1521 of the covering 1505. Both the fifth cable segment 1518 and the fifth tube guide 1540 may extend from the medial bottom strap 1552 to the cable tightening mechanism 1510. In some embodiments, a fourth exposed loop portion 1511 may extend from the medial bottom strap 1552 between the fourth cable segment 1520 and the fifth cable segment 1518.

As can be seen in FIG. 15, some embodiments may include a back strap 1560. In some embodiments, the back strap 1560 may extend along the medial side edge 1572 of the covering 1505. In some embodiments, the back strap 1560 may be tucked between the wearer's leg and/or ankle and the lateral side 1502 of the covering 1505 when the covering 1505 is being placed around the article of footwear 1534. The back strap 1560 may provide a contact surface for the second exposed loop portion 1506 and third exposed loop portion 1515 when the covering 1505 is being worn. In other embodiments the back strap 1560 may extend from the lateral side edge 1570, and may be tucked between the wearer's leg and/or ankle and the medial side 1503 of the covering 1505.

Some embodiments may include one or more loop receiving members that are adapted to receive the exposed loop portions. For example, referring to FIG. 15, some embodiments may include a first loop receiving member 1580 that may be adapted to receive the second exposed cable loop 1506. In some embodiments, the first loop receiving member 1580 may be associated with the medial side edge 1572 on the bottom portion 1578 of the covering 1505. The first loop receiving member 1580 may be attached to the outer surface 1521 of the covering 1505 by any manner known in the art. In some embodiments, the first loop receiving member 1580 may be similar in nature and purpose as discussed in the embodiments associated with FIGS. 12-13.

Referring to FIG. 14, some embodiments may include a second loop receiving member 1584 that may be adapted to receive the third exposed cable loop 1515. In some embodiments, the second loop receiving member 1584 may be located adjacent to the lateral side edge 1570 and the top edge 1574 on the top portion 1576 of the covering 1505. The second loop receiving member 1584 may be attached to the outer surface 1521 of the covering 1505 by any means known in the art. In some embodiments, the second loop receiving member 1584 may be similar in nature and purpose as discussed in the embodiments associated with FIGS. 12-13.

Figure 18:
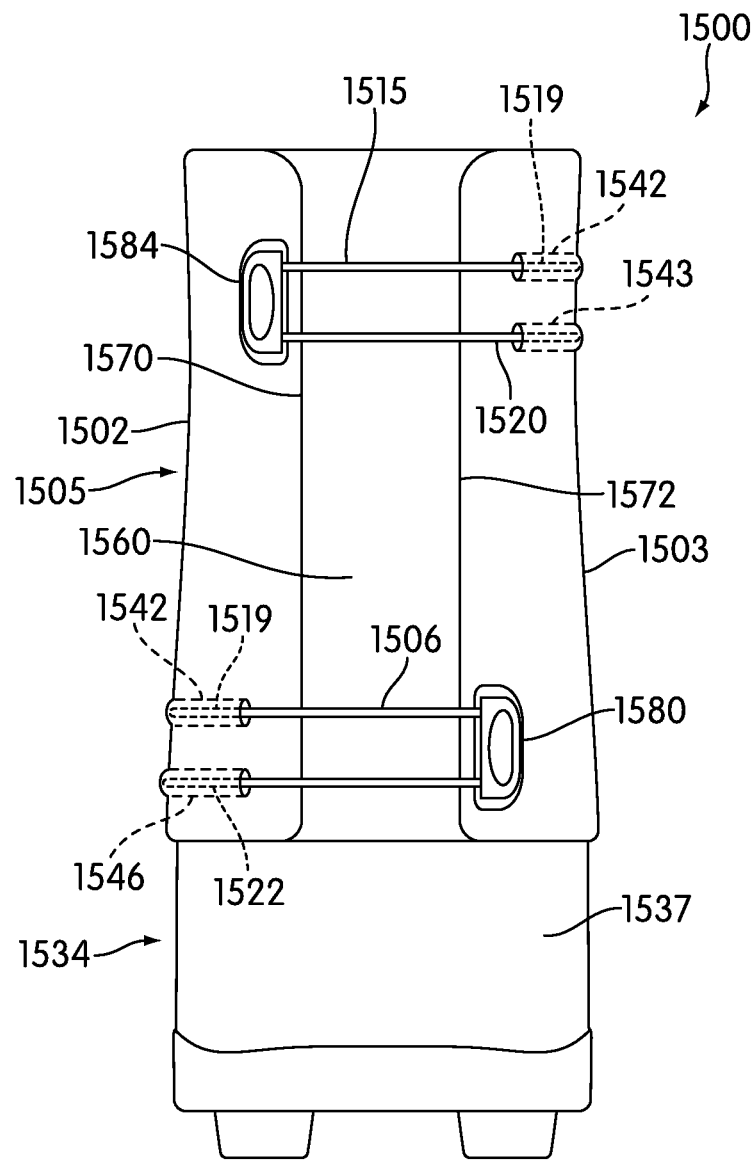
FIG. 18 is a rear view of the ankle support system shown in FIGS. 16 and 17.

FIG. 18 is a rear view of the ankle support system 1500 once the covering 1505 has been placed over the article of footwear 1534. As can be seen in FIG. 18, the second exposed cable loop 1506 has been positioned around the first loop receiving member 1580. In addition, the third exposed cable loop 1515 has been positioned around the second loop receiving member 1584. The back strap 1560 may provide a contact surface for the second exposed cable loop 1506 and third exposed cable loop 1515 in the event that the medial side edge 1572 is not flush with the lateral side edge 1570 of the covering 1570.

Figure 16:
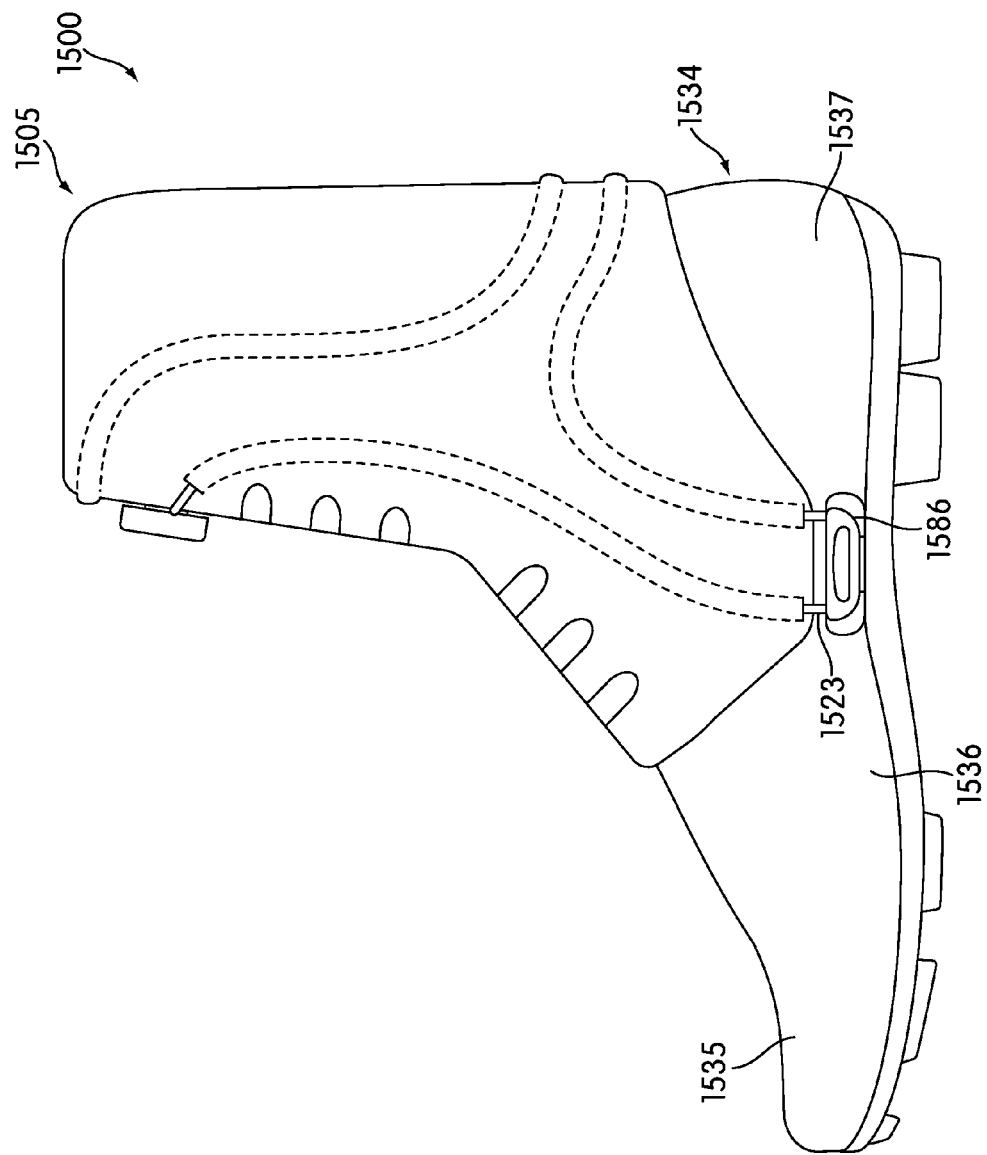
FIG. 16 is a lateral side view of one embodiment of an ankle support system, including the covering shown in FIGS. 14 and 15.

FIG. 16 shows a lateral side view of the ankle support system 1500. An exemplary embodiment may include one or more footwear loop anchors located on a surface of the upper of the article of footwear that may be adapted to receive the exposed cable loops associated with the covering 1505 to secure the covering 1505 to the article of footwear 1534. In an exemplary embodiment, footwear loop anchors include a structure extending outwardly from an outer surface of an upper of an article of footwear. The footwear loop anchors may be attached to the outer surface of the upper of the article of footwear 1534 by any means known in the art. In some embodiments, the diameter of the distal end of the footwear loop anchor may be larger than the diameter of other portions of the footwear loop anchor to assist in retaining the cable around the footwear loop anchor. With this arrangement, the footwear loop anchor may be configured to secure covering 1505 to the article of footwear 1534.

Referring to FIG. 16, in this embodiment, a first footwear loop anchor 1586 may be adapted to receive the first exposed cable loop 1523. In some embodiments, the first footwear loop anchor 1586 may be located on the lateral side of the midfoot region 1536 of the upper of the article of footwear 1534. The first footwear loop anchor 1586 may be attached to the upper of the article of footwear 1534 by any means known in the art. Although FIG. 16 shows the first footwear loop anchor 1586 located in the midfoot region 1536, other embodiments may have the first footwear loop anchor 1586 attached to the forefoot region 1535 or the heel region 1537. In some embodiments, first footwear loop anchor 1586 may be similar in nature and purpose as discussed with reference to the loop receiving members in the embodiments associated with FIGS. 12-13. In other embodiments, first footwear loop anchor 1586 may be similar in nature and purpose as the embodiments discussed later in FIGS. 19-20.

Figure 17:
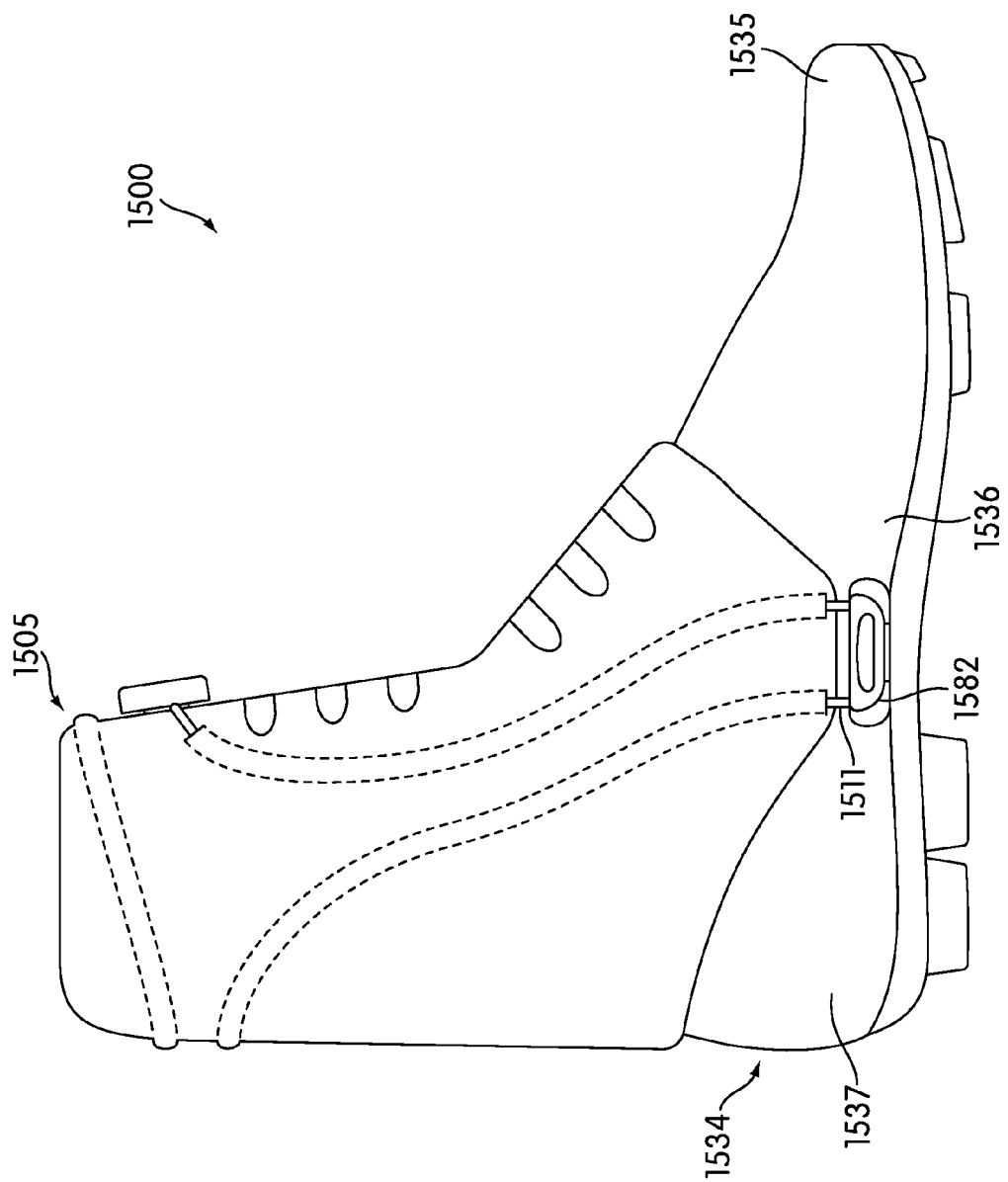
FIG. 17 is a medial side view of the ankle support system shown in FIG. 16.

FIG. 17 shows a medial side view of the ankle support system 1500. Referring to FIG. 17, some embodiments may include a second footwear loop anchor 1582 that may be adapted to receive the fourth exposed cable loop 1511. In some embodiments, the second footwear loop anchor 1582 may be located on the medial side of the midfoot region 1536 of the upper of the article of footwear 1534. The second footwear loop anchor 1582 may be attached to the upper of the article of footwear 1534 by any means known in the art. Although FIG. 17 shows the second footwear loop anchor 1582 located in the midfoot region 1536, other embodiments may have the second footwear loop anchor 1582 attached to the forefoot region 1535 or the heel region 1537. In some embodiments, second footwear loop anchor 1582 may be similar in nature and purpose as discussed with reference to the loop receiving members in the embodiments associated with FIGS. 12-13. In other embodiments, second footwear loop anchor 1582 may be similar in nature and purpose as the embodiments discussed later in FIGS. 19-20.

Some embodiments may include provisions for positioning the exposed loop portions around the loop receiving members and/or footwear loop anchors. For example, some embodiments may include pull-tabs attached to the exposed loop portions. Referring to FIGS. 14-15, pull-tabs may be fixedly attached to each of the exposed loop portions. FIG. 14 shows a first pull-tab 1591 attached to first exposed loop portion 1523, and a second pull-tab 1590 attached to second exposed loop portion 1506. FIG. 15 shows a third pull-tab 1592 attached to a third exposed loop portion 1515, and a fourth pull-tab 1593 attached to a fourth exposed loop portion 1511. In some embodiments, pull-tabs may be manufactured from any fabric or material known in the art. In some embodiments, each pull-tab may be attached to each exposed loop portion by any method known in the art. In some embodiments, each pull-tab may include a loop through which the exposed loop portion may extend. In other embodiments, each pull-tab may be adhered or sewn onto each exposed loop portion.

Some embodiments of an ankle support system 1500 may include provisions for adjusting the tightness of the covering 1505 once the covering 1505 has been arranged into a closed condition around the article of footwear. In some embodiments, the cable 1516 may be slidably engaged with the covering 1505 and may be tightened using a tightening mechanism 1510 in order to adjust the desired tension. The cable 1516 may be made of any material known in the art, such as metals, textiles, fiber components, or the like. The cable 1516 may have any size or shape known in the art, for example, a single filament, separate filaments bound or braided together, or may include a flat ribbon of material.

The cable tightening mechanism 1510 in some embodiments may vary. In some embodiments, the cable tightening mechanism 1510 shown in FIGS. 14-18 may have similar properties and characteristics as the cable tightening mechanism 110 described in FIGS. 1-7. However, as will be discussed in FIGS. 21-23, the cable tightening mechanism 1510 may also include a removable cam lever system. In some embodiments, the cable tightening mechanism 1510 may be associated with the cable 1516 in the same manner as the cable tightening mechanism 110 associates with cable 117 in FIGS. 1-7.

The ankle support system 1500 operates similar to the ankle support system 100 discussed in FIGS. 1-7. For example, in some embodiments, the ankle support system 1500 may include an article of footwear 1534 as shown in FIGS. 16-18. In one embodiment, the forefoot 1535 of the article of footwear 1534 may be positioned through the back edge 1557, until the forefoot portion 1535 is extending through the front opening 1556 in the covering 1505. Other aspects relating to donning and doffing the covering 1505, are similar to donning and doffing the covering 105 discussed in FIGS. 1-7. Similarly, the methods of tightening and loosening the cables in the ankle support system 1500 may be similar to those discussed in the ankle support system 100 discussed in FIGS. 1-7.

In some embodiments, an ankle support system may include footwear loop anchors attached to the upper of the article of footwear. During athletic activity, the footwear loop anchors attached to the upper of the article of footwear may experience a large magnitude of stress. Therefore, in some embodiments, the article of footwear may include provisions for withstanding large amounts of stress in order to prevent the footwear loop anchors from fracturing and/or breaking free from the article of footwear. For example, in some embodiments, a reinforcement strap may connect the footwear loop anchors with the opposite side of the article of footwear.

Figure 19:
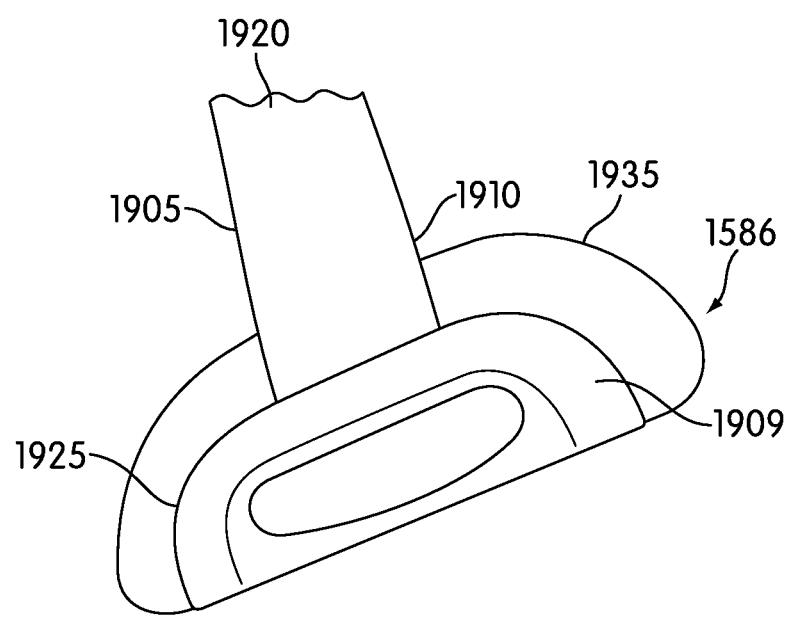
FIG. 19 is a perspective view of one embodiment of a reinforcement strap attached to a footwear loop anchor.
Figure 20:
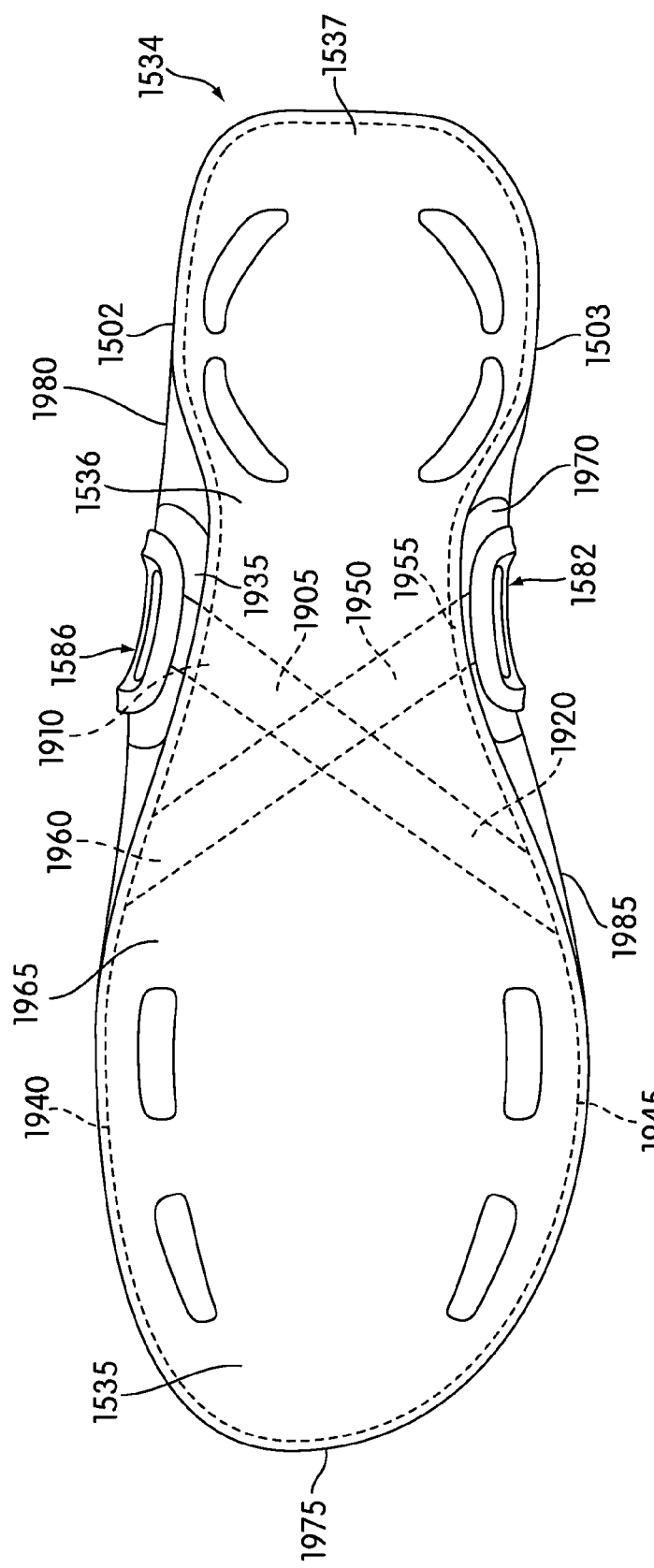
FIG. 20 is a bottom view of one embodiment of athletic footwear having including footwear loop anchors shown in FIG. 19.

FIGS. 19-20 shows one embodiment of footwear loop anchors mounted on an upper of an article of footwear. FIG. 19 shows a reinforcement strap 1905 attached to the first footwear loop anchor 1586 discussed in FIGS. 14-18. Although FIG. 19 relates to the first footwear loop anchor 1586, any footwear loop anchor and/or any loop receiving member discussed in any embodiment herein may have a similar construction and purpose. Referring to FIG. 19, a first reinforcement strap 1905 has a first end 1910 attached to the base 1935 of the first footwear loop anchor 1586. In some embodiments, the first footwear loop anchor 1586 may have a similar structure to the first loop receiving member 1080 discussed in FIGS. 12-13. For example, the first footwear loop anchor 1586 may include an outlaying portion 1925 that is similar to the outlaying portion 1225 discussed in FIGS. 12-13. In addition, the first footwear loop anchor 1586 may have a top surface 1909 similar to the top surface 1205 described in FIGS. 12-13. Other features described with reference to the first loop receiving member 1080 in FIGS. 12-13 may also be present in the first footwear loop anchor 1586.

The first end 1910 of the first reinforcement strap 1905 may be attached to the base 1935 of the first footwear loop anchor 1586 by any manner known in the art. In some embodiments, the first end 1910 may be tied, sewn, anchored, fastened, or adhered to the base 1935. In other embodiments, the first end 1910 may be looped through an opening (not shown in FIG. 19) in the base 1935.

In some embodiments, the second end 1920 of the first reinforcement strap 1905 may be attached to a medial inner surface 1945 of an article of footwear. FIG. 20 shows one embodiment of an article of footwear 1534 incorporating the first footwear loop anchor 1586 discussed in FIG. 19. FIG. 20 shows the first footwear loop anchor 1586 attached to the lateral side 1502 of the upper of the article of footwear 1534 discussed in FIGS. 14-18. FIG. 20 also shows a first reinforcement strap 1905 attached to the first footwear loop anchor 1586. While the first end 1910 of the first reinforcement strap 1905 is attached to the base 1935 of the first footwear loop anchor 1586, the second end 1920 may be attached to a medial inner surface 1945 of the article of footwear 1534. The second end 1920 of the first reinforcement strap 1905 may be attached to the medial inner surface 1945 of the article of footwear 1534 in any manner known in the art, including the methods disclosed for attaching the first end 1910 to the base 1935 of the footwear loop anchor 1586. In some embodiments, the first reinforcement strap 1905 may extend laterally from the lateral side 1502 to the medial side 1503 directly under the wearer's foot. In other embodiments, the first reinforcement strap 1905 may extend across the article of footwear 1534 through a channel (not shown in FIG. 20) in the sole 1965 of the article of footwear 1534. In still further embodiments, the first reinforcement strap 1905 may be embedded within the sole 1965 of the article of footwear 1534 with the sole 1965 molded around the first reinforcement strap 1905.

FIG. 20 also shows the second footwear loop anchor 1582 attached to the medial side 1503 of the upper of the article of footwear 1534, as discussed in FIGS. 14-18. Additionally, FIG. 20 shows a second reinforcement strap 1950 attached to the second footwear loop anchor 1582. While the first end 1955 of the second reinforcement strap 1950 is attached to the base 1970 of the second footwear loop anchor 1582, the second end 1960 may be attached to a lateral inner surface 1940 of the article of footwear 1534. The second end 1960 of the second reinforcement strap 1950 may be attached to the lateral inner surface 1940 of the article of footwear 1534 in any manner known in the art, including the methods disclosed for attaching the first end 1955 to the base 1935 of the second footwear loop anchor 1582. In some embodiments, the second reinforcement strap 1950 may extend generally laterally from the medial side 1503 to the lateral side 1502 directly under the foot. In other embodiments, the second reinforcement strap 1950 may extend across the article of footwear 1534 through a channel (not shown in FIG. 20) in the sole 1965 of the article of footwear 1534. In still further embodiments, the second reinforcement strap 1950 may be embedded within the sole 1965 of the article of footwear 1534 with the sole 1965 molded around the second reinforcement strap 1950.

In some embodiments, as shown in FIG. 20, the second end 1920 of the first reinforcement strap 1905 may be attached to the medial inner surface 1945 at a point that is closer to the tip of the toe 1975 than the first end 1910 of first reinforcement strap 1905. Similarly, the second end 1960 of the second reinforcement strap 1950 may be attached to the lateral inner surface 1940 at a point that is closer to the tip of the toe 1975 than the first end 1955 of the second reinforcement strap 1950. This arrangement may cause the first reinforcement strap 1905 to cross the second reinforcement strap 1950, forming an X pattern as shown in FIG. 20.

In some embodiments, the location of the attachment point of the second end 1920 of the first reinforcement strap 1905 may vary. For example, the second end 1920 of the first reinforcement strap 1905 may be attached to a medial inner surface 1945 anywhere along the forefoot region 1535, midfoot region 1536, or heel region 1537 of the article of footwear 1534.

In some embodiments, the location of the attachment point of the first footwear loop anchor 1586 may vary. For example, the first footwear loop anchor 1586 may be attached to an outer lateral surface 1980 of the upper anywhere along the forefoot region 1535, midfoot region 1536, or heel region 1537 of the article of footwear 1534.

In some embodiments, the location of the attachment point of the second end 1960 of the second reinforcement strap 1950 may vary. For example, the second end 1960 of the second reinforcement strap 1950 may be attached to a lateral inner surface 1940 anywhere along the forefoot region 1535, midfoot region 1536, or heel region 1537 of the article of footwear 1534.

In some embodiments, the location of the attachment point of the second footwear loop anchor 1582 may vary. For example, the second footwear loop anchor 1582 may be attached to an outer medial surface 1985 of the upper anywhere along the forefoot region 1535, midfoot region 1536, or heel region 1537 of the article of footwear 1534.

In other embodiments, an ankle support system may include loop receiving members attached to the sole structure of the article of footwear. In some cases, loop receiving members may be attached to the sole structure of the article of footwear in any manner known in the art. In other cases, one or more loop receiving members may be integrally formed with the sole structure of the article of footwear. With this arrangement, loop receiving members may be further secured to the article of footwear.

Figure 21:
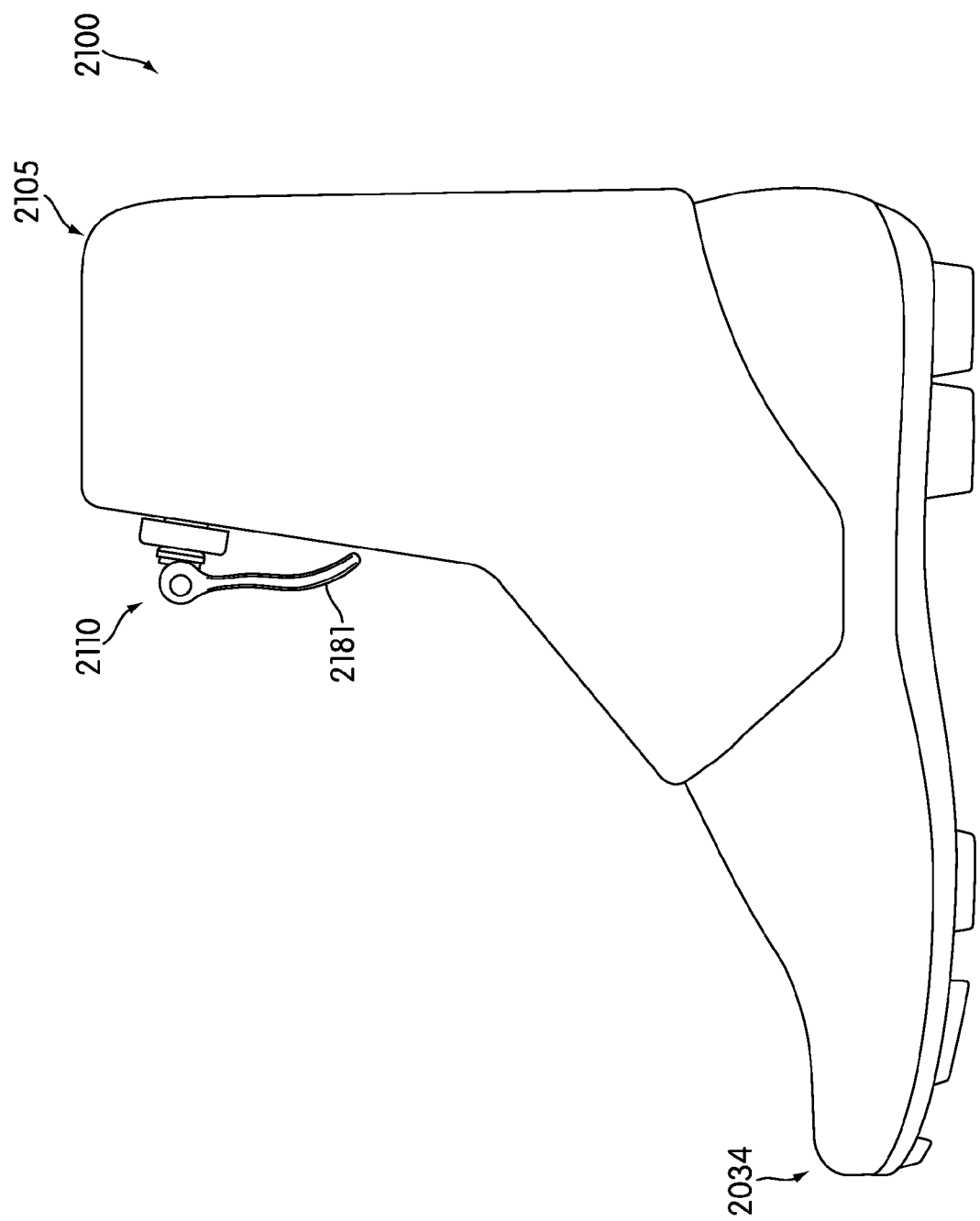
FIG. 21 is a lateral side view of one embodiment of an ankle support system including a removable cam lever locking mechanism.
Figure 22:
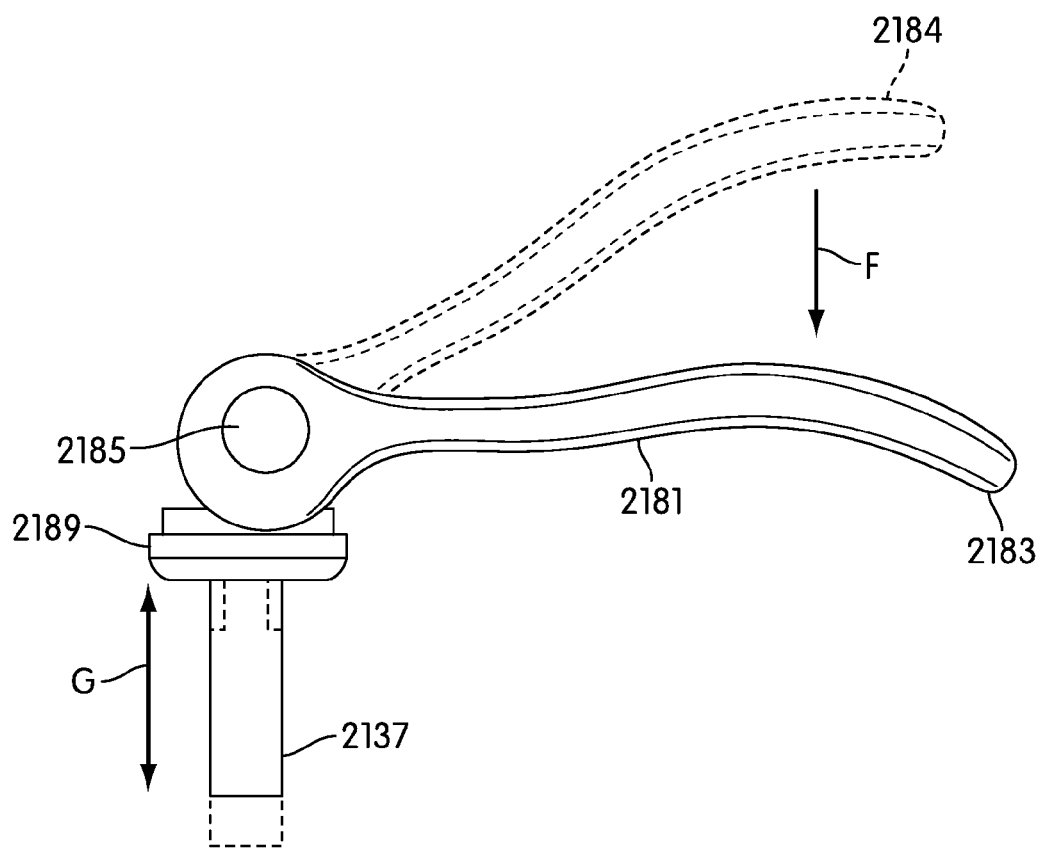
FIG. 22 is an enlarged side view of one embodiment of a cam lever locking mechanism for securing cable once an ankle support system has been properly positioned.
Figure 23:
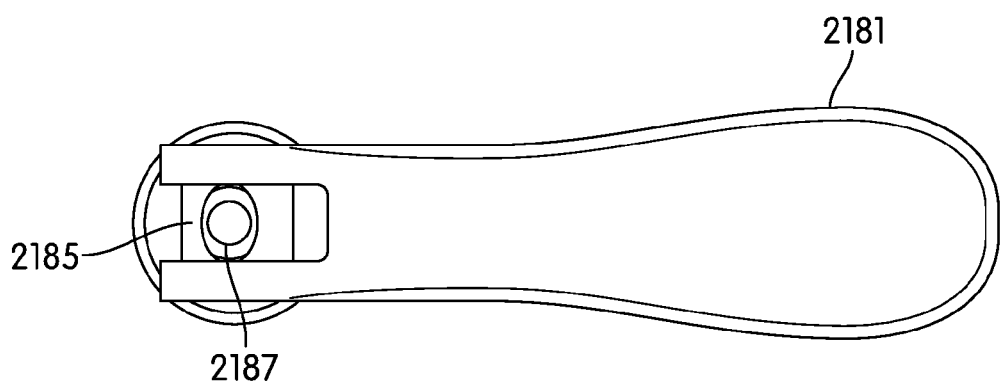
FIG. 23 is a top view of the cam lever locking mechanism shown in FIG. 22.

In some embodiments, a locking mechanism may be used to lock a cable in position to maintain the desired length. FIG. 2 shows an embodiment of how a spindle 237 may be locked in position by ratcheting the spindle 237 so that the desired length of the cable may be maintained. In other embodiments, the locking mechanism may be a mechanical locking mechanism. Referring to FIGS. 21-23, the locking mechanism may be a removable cam lever system 2110. The removable cam lever system 2110 may be used on any of the embodiments discussed in FIGS. 1-20.

FIGS. 21-23 show an embodiment of an ankle support system 2100 including a covering 2105 and article of footwear 2034. In some embodiments the covering 2105 may have a removable cam lever system 2110 as the locking mechanism. The removable cam lever system 2110 may be any type of a cam lever known in the art. In some embodiments, removable cam lever system 2110 may be associated with a mechanism to wind cable. Referring to FIGS. 22-23, in some embodiments, a cam lever 2181 may be attached to a spindle 2137 to wind cable. In some embodiments, spindle 2137 may be rotated to wind cable and thereby tighten the covering 2105 about the article of footwear 2034. Spindle 2137 may also be rotated in an opposite direction to unwind the cable.

Spindle 2137 may be disposed anywhere on the surface of the covering 2105. In some embodiments, the spindle 2137 may be disposed on the front of the covering 2105. In other embodiments, the spindle 2137 may be disposed on the lateral side of the covering 2105. The spindle 2137 may be located in any location discussed in the embodiments shown in FIGS. 1-20.

In some embodiments, cam lever 2181 may lock spindle 2137 in position so that the desired length of cable may be maintained. In some embodiments, cam lever 2181 may lock spindle 2137 by applying friction to spindle 2137. In some embodiments, cam lever 2181 may lock spindle 2137 by causing spindle 2137 to be pressed against a friction causing surface. A friction causing surface may be a stopper, such as stopper 2189. In one embodiment shown in FIGS. 22 and 23, cam lever 2181 may cause spindle 2137 to be pressed against stopper 2189. In some embodiments, the cam lever 2181 may be removed once the spindle 2137 is locked.

FIGS. 22-23 show one embodiment of cam lever 2181 attached to spindle 2137. The workings of this embodiment will now be explained. Other cam levers, using other leverage methods, may also be used.

Cam lever 2181 may have pin 2187 connected to spindle 2137. Pin 2187 and spindle 2137 may be configured to move along a common axis. The common axis may be any axis. In some embodiments, the common axis may be the G axis. FIG. 22 shows one embodiment where the common axis is the G axis that is labeled G. Pin 2187 and spindle 2137 may be configured to move along the G axis from a locked position 2183 (shown in solid lines in FIG. 22) to an unlocked position 2184 (shown in dotted lines in FIG. 22). In the locked position 2183, spindle 2137 may be prevented from rotating around the common axis and the desired length of cable may be maintained. In the locked position 2183, the cam lever 2181 may be removed in order to reduce the profile of the removable cam lever system 2110. In the unlocked position 2184, spindle 2137 may rotate around the common axis to wind and unwind cable.

In some embodiments, cam lever 2181 may be connected to pin 2187. Cam lever 2181 may rotate about axle 2185. Cam lever 2181 may rotate from an open position 2184 (shown in dotted lines in FIG. 22) to a closed position 2183 (shown in solid lines in FIG. 22) by a use applying force F. Rotating cam lever 2181 may move spindle 2137 and pin 2187 from the locked position to the unlocked position along the G axis. When at the open position, spindle 2137 may be in an unlocked position and cam lever 2183 may rotate around axle 2185 to turn spindle 2137 in a direction that will wind cable or to turn spindle 2137 in an opposite direction that will unwind cable. When at the closed position, spindle 2137 may be in a locked position and cam lever 2181 may be prevented from rotating around axle 2185 so that the desired length of cable may be maintained. When in a closed position, cam lever 2181 may be removed in order to reduce the profile of the removable cam lever system 2110.

In some embodiments, pin 2187 may be used as a cable tightening device, instead of spindle 2137. In some embodiments, cable may be directly attached to pin 2187. Moving pin 2187 to a locked position may cause cable to be pulled tight and moving pin 2187 to an unlocked position may cause cable to be released. Pin 2187 may be moved along the G axis to the locked and unlocked position by rotating cam lever 2181 along axle 2185 to the closed position and open position, respectively, by a user applying force F. Pin 2187 may move upward along the G axis to the locked position from the unlocked position when cam lever 2181 is rotated along axle 2185 to the closed position by a user applying force F. When the pin 2187 is locked, the cam lever 2181 may be removed in order to reduce the profile of the removable cam lever system 2110. Once the cam lever 2181 has been reattached, pin 2187 may move downward along the G axis to the unlocked position when cam lever 2181 is rotated along axle 2185 to the open position by a user applying an opposing force F.

While various embodiments of the ankle support system have been described, the description is intended to be exemplary, rather than limiting and it will be apparent to those of ordinary skill in the art that many more embodiments and implementations are possible that are within the scope of the current embodiments. Accordingly, the embodiments are not to be restricted except in light of the attached claims and their equivalents. Also, various modifications and changes may be made within the scope of the attached claims. Any of the features described in any one embodiment herein may also be include in any other embodiment described herein.

What is claimed is:

1. An ankle and foot support system comprising:
a covering configured to be removably wrapped around a portion of an article of footwear, the covering having an outer surface;
the covering having a one piece construction and including a lateral portion having a first edge and a medial portion having a second edge, wherein the covering is configured to encircle an ankle of a wearer of the support system such that the first edge of the lateral portion and the second edge of the medial portion abut one another in a rear portion of the ankle;
a tube guide attached to the outer surface of the covering;
a cable tightening mechanism attached to the outer surface of the covering; and
a cable wherein a first portion of the cable is slidably engaged with the tube guide, a second portion of the cable is associated with the cable tightening mechanism, a third portion of the cable forms a first exposed loop extending from the first edge of the lateral portion of the covering; and a fourth portion of the cable forms a second exposed loop extending from the second edge of the medial portion of the covering;
a first loop receiving member attached to the outer surface of the covering proximate to the second edge of the medial portion of the covering, wherein the first loop receiving member is configured to removably receive the first exposed loop; and
a second loop receiving member attached to the outer surface of the covering proximate to the first edge of the lateral portion of the covering, wherein the second loop receiving member is configured to removably receive the second exposed loop.

2. The ankle and foot support system of claim 1, wherein the cable tightening mechanism is disposed in a front region of the covering configured to be associated with a front portion of a foot of a wearer of the support system.

3. The ankle and foot support system of claim 2, further including a second tube guide attached to the outer surface of the covering and extending across the front region of the covering.

4. The ankle and foot support system of claim 3, wherein the second tube guide is disposed in a higher location than the cable tightening mechanism when the support system is worn by a wearer.

5. The ankle and foot support system of claim 1, wherein the first exposed loop and the first loop receiving member are disposed on an upper portion of the covering, and the second exposed loop and the second loop receiving member are disposed on a lower portion of the covering.

6. The ankle and foot support system of claim 1, wherein the cable includes a first end and a second end, wherein the first end is attached to the second end.

7. The ankle and foot and foot support system of claim 1, wherein the covering includes a cut out portion to provide for ventilation.

8. An ankle and foot support system comprising:
an article of footwear including an upper and a sole structure secured to the upper, the article of footwear having a lateral side and a medial side;
a covering having a one piece construction and being configured to be removably wrapped around a portion of the article of footwear, the covering having an outer surface;
wherein the covering is configured to encircle an ankle of a wearer of the support system such that a first edge of a first portion of the covering and a second edge of a second portion of the covering abut one another in a rear portion of the ankle;
a cable tightening mechanism attached to the outer surface of the covering; and
a cable, wherein a first portion of the cable is slidably engaged with the covering, wherein a second portion of the cable is associated with the cable tightening mechanism;
wherein a third portion of the cable forms a first exposed loop, and a fourth portion of the cable forms a second exposed loop; and
wherein the article of footwear includes a first loop receiving member disposed on the lateral side of the article of footwear and configured to removably receive the first exposed loop of the cable, and a second loop receiving member disposed on the medial side of the article of footwear and configured to removably receive the second exposed loop.

9. The ankle and foot support system of claim 8, wherein the cable tightening mechanism is disposed in a region of the covering configured to be associated with a front portion of the article of footwear.

10. The ankle and foot support system of claim 9, further including a first tube guide attached to the outer surface of the covering, wherein a first portion of the cable is slidably engaged with the first tube guide.

11. The ankle and foot support system of claim 10, wherein the first tube guide is disposed in a higher location than the cable tightening mechanism when the support system is worn by a wearer.

12. The ankle and foot support system of claim 8, wherein the cable includes a first end and a second end, wherein the first end is attached to the second end.

13. The ankle and foot support system of claim 8, wherein a fifth portion of the cable forms a third exposed loop extending from the first edge of the first portion of the covering; and a sixth portion of the cable forms a fourth exposed loop extending from the second edge of the second portion of the covering;
the system further including a third loop receiving member attached to the outer surface of the covering proximate to the second edge of the second portion of the covering, wherein the third loop receiving member is configured to removably receive the third exposed loop; and
a fourth loop receiving member attached to the outer surface of the covering proximate to the first edge of the first portion of the covering, wherein the fourth loop receiving member is configured to removably receive the fourth exposed loop.

14. The ankle and foot support system of claim 8, wherein the covering includes a cut out portion to provide for ventilation.

15. A method of providing support to an ankle and foot comprising:
- removably positioning a covering having a one piece construction over a portion of an article of footwear such that the covering is configured to encircle an ankle of a wearer of the article of footwear such that a first edge of a lateral portion of the covering and a second edge of a medial portion of the covering abut one another in a rear portion of the article of footwear;
- slidably engaging at least a first portion of a cable with the covering, the cable further including a second portion associated with a cable tightening system, a third portion forming a first exposed loop extending from the first edge of the lateral portion of the covering; and a fourth portion forming a second exposed loop extending from the second edge of the medial portion of the covering;
- removably positioning the first exposed loop on a first loop receiving member attached to the outer surface of the covering proximate to the second edge of the medial portion of the covering; and removably positioning the second exposed loop on a second loop receiving member attached to the outer surface of the covering proximate to the first edge of the lateral portion of the covering; and
- adjusting the covering about the article of footwear by adjusting the cable tightening mechanism.

16. The method of claim 15, further comprising:
a first tube guide attached to the outer surface of the covering, wherein a portion of the cable is slidably engaged with the first tube guide.

17. The method of claim 15, wherein the cable tightening mechanism is disposed in a front region of the covering configured to be associated with a front portion of a foot of a wearer of the support system.

18. The method of claim 17, further including a second tube guide attached to the outer surface of the covering and extending across the front region of the covering.

19. The method of claim 18, wherein the second tube guide is disposed in a higher location than the cable tightening mechanism when the support system is worn by a wearer.

20. The method of claim 15, wherein the cable includes a first end and a second end, wherein the first end is attached to the second end.

* * * * *